(12) United States Patent
Deng et al.

(10) Patent No.: US 8,791,262 B2
(45) Date of Patent: Jul. 29, 2014

(54) ASYMMETRIC FRIEDEL-CRAFTS ALKYLATIONS CATALYZED BY BIFUNCTIONAL CINCHONA ALKALOIDS

(75) Inventors: Li Deng, Newton Lower Falls, MA (US); Hongming Li, Scotch Plains, NJ (US)

(73) Assignee: Brandeis University, Waltham, MA (US)

( * ) Notice: Subject to any disclaimer, the term of this patent is extended or adjusted under 35 U.S.C. 154(b) by 1297 days.

(21) Appl. No.: 12/095,843

(22) PCT Filed: Dec. 1, 2006

(86) PCT No.: PCT/US2006/045960
§ 371 (c)(1),
(2), (4) Date: Oct. 14, 2008

(87) PCT Pub. No.: WO2007/064861
PCT Pub. Date: Jun. 7, 2007

(65) Prior Publication Data
US 2009/0203913 A1    Aug. 13, 2009

Related U.S. Application Data

(60) Provisional application No. 60/742,102, filed on Dec. 2, 2005, provisional application No. 60/781,624, filed on Mar. 13, 2006.

(51) Int. Cl.
*C07D 453/04*    (2006.01)
(52) U.S. Cl.
USPC .............................................. 546/134
(58) Field of Classification Search
USPC .............................................. 546/134
See application file for complete search history.

(56) References Cited

U.S. PATENT DOCUMENTS

| | | | |
|---|---|---|---|
| 1,720,462 | A | 7/1929 | Blagden |
| 2,072,004 | A | 2/1937 | Lutz |
| 2,377,814 | A | 6/1945 | Schnider |
| 2005/0043353 | A1 | 2/2005 | Deng |

FOREIGN PATENT DOCUMENTS

| | | | |
|---|---|---|---|
| WO | WO-02/05953 | A2 | 1/2002 |
| WO | WO-03/011799 | A1 | 2/2003 |
| WO | WO-03/018549 | A2 | 3/2003 |

OTHER PUBLICATIONS

Marco Bandini Chapter 1 "General Aspects and Historical Background" in "Catalytic Asymmetric Friedel-Crafts Alkylations" 2009, Wiley-VCH, 1-16.*
Torok et. al. "Highly Enantioselective Organocatalytic Hydroxyalkylation of Indoles with Ethyl Trifluoropyruvate" Angew. Chem. Int. Ed. Apr. 21, 2005, 44, 3086-3089.*
Barnes, D. M. et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", J. Am. Chem. Soc., 124:13097-13105 (2002).
Berner, O. M. et al., "Asymmetric Michael Additions to Nitroalkenes", Eur. J. Org. Chem., 1877-1894 (2002).
Brunner, H. et al., "α-Amino Acid Derivatives by Enantioselective Decarboxylation", XP-002399850 Eur. J. Org. Chem. 2854-2862 (2003).
Brunner, H. et al., "Asymmetric Catalysis, CIII[1]: Enantioselective Michael Addition of 1,3-Dicarbonyl Compounds to Conjugated Nitroalkenes", Monatshefte für Chemie, 127:1063-1072 (1996).
Brunner, H. et al., "Asymmetric Catalysis, 131 Naproxen Derivatives by Enantioselective Decarboxylation", XP-002399851 Eur. J. Org. Chem. 2119-2133 (2000).
Calter, M. A., "Catalytic, Asymmetric Dimerization of Methylketene", J. Org. Chem., 61:8006-8007 (1996).
Li, B.-J. et al., "Asymmetic Michael Addition of Arylthiols to α,β-Unsaturated Carbonyl Compounds Catalyzed by Bifunctional Organocatalysts", XP-002399853 Synlett 4: 0603-0606 (2005).
Chen, Y, et al., "Asymmetric Alcoholysis of Cyclic Anhydrides", Chem. Rev., 103:2965-2983 (2003).
Cortez, G. S. et al., "Bicyclic β-Lactones via Intramolecular NCAL Reactions with Cinchona Alkaloids: Effect of the C9-Substituent on Enantioselectivity and Catalyst Conformation", Synthesis, 11:1731-1736 (2001).
Cortez, G. S. et al., "Intramolecular, Nucleophile-Catalyzed Aldol-Lactonization (NCAL) Reactions: Catalytic, Asymmetric Synthesis of Bicyclic β-Lactones", J. Am. Chem. Soc., 123:7945-7946 (2001).
France, S. et al., "Nucleophilic Chiral Amines as Catalysts in Asymmetric Synthesis", Chem. Rev., 103:2985-3012 (2003).
Gröger, H., "The Development of New Monometallic Bifunctional Catalysts with Lewis acid and Lewis Base Properties, and their Application in Asymmetric Cyanation Reactions", Chem. Eur. J., 7(24):5247-5251 (2001).
Hiemstra, H. et al., "Addition of Aromatic Thiols to Conjugated Cycloalkenones, Catalyzed by Chiral β-Hydroxy Amines. A Mechanistic Study on Homogeneous Catalytic Asymmetric Synthesis", J. Am. Chem. Soc., 103:417-430 (1981).
Iwabuchi, Y. et al., "Chiral Amine-Catalyzed Asymmetric Baylis-Hillman Reaction: A Reliable Route to Highly Enantiomerically Enriched (a-Methylene-β-hydroxy)esters", J. Am. Chem. Soc., 121:10219-10220 (1999).
Ji, J. et al., "Catalytic Enantioselective Conjugate Addition of 1,3-Dicarbonyl Compounds to Nitroalkenes", J. Am. Chem. Soc., 121:10215-10216 (1999).

(Continued)

*Primary Examiner* — David K O Dell
(74) *Attorney, Agent, or Firm* — Foley Hoag LLP

(57) ABSTRACT

In certain embodiments, the present invention relates to methods for asymmetric Friedel-Crafts alkylation catalyzed by bifunctional cinchona alkaloids. In certain embodiments, the catalyst is a 6'-OH cinchona alkaloid. In certain embodiments, the electrophile is an α-ketoester or aldehyde. In certain embodiments, the nucleophile is an aromatic heterocycle. In certain embodiments, the nucleophile is an aromatic N-containing heterocycle. In certain embodiments, the nucleophile is an indole. In certain embodiments, the methods of the invention are relatively insensitive to concentration, temperature, air and moisture.

20 Claims, 8 Drawing Sheets

(56) References Cited

OTHER PUBLICATIONS

Kawahara, S. et al., "β-Isocupreidine-Catalyzed Asymmetric Baylis-Hillman Reaction of (mines", Organic Letters, 5(17):3103-3105 (2003).
Li, H. et al., "Organocatalytic enantioselective Michael addition of thioacetic acid to enones", XP-002399859 Tetrahedron Letters 47: 3145-3148 (2006).
Li, H. et al., "Stereocontrolled Creation of Adjacent Quaternary and Tertiary Stereocenters by a Catalytic Conjugate Addition", XP-002344994, Angew Chem. Int. Ed. 44: 105-108 (2005).
Li, H. et al., "Catalytic Enantioselective C-C Bond Forming Conjugate Additional with Vinyl Sulfones", J. Am. Chem. Soc., 127:8948-8949 (2005).
Li, H. et al., "Highly Enantioselective Conjugate Addition of Malonate and β-Ketoester to Nitroalkenes: Asymmetric C-C Bond Formation with New Bifunctional Organic Catalysts Based on Cinchona Alkaloids", J. Am. Chem. Soc., 126:9906-9907 (2004).
List, B., "Asymmetric Aminocatalysis", Synlett, 11:1675-1686 (2001).
List, B., "Proline-catalyzed asymmetric reactions", Tetrahedron, 58:5573-5590 (2002).
Liu, T.Y. et al., "Enantioselective construction of Quaternary carbon centre catalysed by bifunctional organocatalyst", XP-002399858 Org. Biomol. Chem. 4: 2097-2099 (2006).
Liu, X. et al., "Highly Enantioselective Amination of a-Substituted a-Cyanoacetates with Chiral Catalysts Accessible from Both Quinine and Quinidine", Organic Letters, 7(2):167-169 (2005).
Ma, D. et al., "Diastereoselective Henry reactions of N,N-dibenzyl χ-amino aldehydes with nitromethane catalyzed by enantiopure guanidines", XP-002399848 Tetrahedron Letters 43: 9401-9403 (2002).
Marcelli, T. et al., "Cinchona Derivatives as Bifunctional Organocatalysts for the Direct Asymmetric Nitroaldol (Henry) Reaction", Synlett., 18:2817-2819 (2005).
McCooey, S. et al., "Urea- and Thiourea-Substituted Chinchona Alkaloid Derivatives as Highly Efficient Bifunctional Organocatalysts for the Asymmetric Addtion of Malonate to Nitroalkenes: Inversion of Configuration at C9 Dramatically Improves Catalyst Performance" XP-002399854 Angew Chem. Int. Ed. 44: 6367-6370 (2005).
Okino, T. et al., "Enantioselective Michael Reaction of Malonates to Nitroolefins Catalyzed by Bifunctional Organocatalysts", J. Am. Chem. Soc., 125:12672-12673 (2003).
Rogers, L. M.-A. et al., "Enantioselective decarboxylation-reprotonation of an a-amino malonate derivative as a route to optically enriched cyclic a-amino acid", Tetrahedron Letters, 44:3047-3050 (2003).
Shibasaki, M. et al., "Asymmetric Catalysis with Heterobimetallic Compounds", Angew. Chem. Int. Ed. Engl., 36:1236-1256 (1997).
Shibasaki, M. et al., "Lanthanide Complexes in Multifunctional Asymmetric Catalysis", Chem. Rev., 102:2187-2209 (2002).
Sibi, M. P. et al., "Enantioselective Conjugate Additions", Tetrahedron, 56:8033-8061 (2000).

Song, J. et al., The Mannich Reaction of Malonates with Simple (mines Catalyzed by Bifunctional Cinchona Alkaloids: Enantioselective Synthesis of β-Amino Acids, XP-002399857 J. Am. Chem. Soc. 128: 6048-6049 (2006).
Suzko, J. et al., "B-Isoquinine and niquine", *Roczniki Chemii*, 5:358-385 (1925).
Taggi, A. E. et al., "Catalytic, Asymmetric Synthesis of β-Lactams", J. Am. Chem. Soc., 122:7831-7832 (2000).
Tian, S-K, et al., "Asymmetric Organic Catalysis with Modified Cinchona Alkaloids", Acc. Chem. Res. (abstract), Dec 10 2003.
Tillman, A. L. et al., "Direct enantio- and diastereoselective Mannich reactions of malonate and β-keto esters with N-Boc and N-Cbz aldimines catalysed by a bifunctional cinchonine derivative", XP-002399856 Chem. Commun. 1191-1193 (2006).
Vakulya, B. et al., "Highly Enantioselective Conjugate Addition of Nitromethane to Chalcones Using Bifunctional Cinchona Organocatalysts", XP002399852 Organic Letters 7(10): 1967-1969 (2005).
Wack, H. et al., "Catalytic, Asymmetric a-Halogenation", J. Am. Chem. Soc., 123:1531-1532 (2001).
Wynberg, H., Asymmetric Catalysis by Alkaloids, Department of Chemistry, University of Groningen, The Netherlands, 88-127.
Wynberg, H., "Asymmetric Catalysts by Alkaloids", Top. Stereochem., 16:87-129 (1986).
Ye, J. et al., Enantioselective Organocatalytic Michael addition of malonate esters to nitro olefins using bifunctional cinchonine derivatives XP-002399855 Chem. Commun. 4481-4483 (2005).
Blaser, H.U. et al., "Heterogeneous Enantioselective Hydrogpenation of Ethyl Pyruvate Catalyzed by Cinchona-Meodified Pt Catalysts: Effect of Modifier Structure," J. Am. Chem. Soc. 122:12675-12682 (2000).
Brunner, H. et al., "Enantioselective Catalysis. Part 133: Conformational Analysis of Amides of 9-amino(9-deoxy)epicinchonine," Tetrahedron: Asymmetry 11:1501-1512 (2000).
Brunner, H. et al., "Enantioselective Catalysis 98. Preparation of 9-Amino(9-deoxy)cinchona Alkaloids," Tetrahedron: Asymmetry 6(7):1699-1702 (1995).
Czerwenka, C. et al., "Direct High-Performance Liquid Chromatographic Separation of Peptide Enantiomers: Study on Chiral Recognition by Systematic Evaluation of the Influence of Structural Features of the Chiral Selectors on Enantioselectivity," Analytical Chemistry 74:5658-5666 (2002).
Deady, L.W. et al., "A Cinchonidine Derivative for Photoaffinity Labelling of Proteins," Journal of Labelled Compounds and Radiopharmaceuticals 43:977-981 (2002).
Cowman, a.F. et al., "Synthesis and Activity of Some Antimalarial Bisquinolinemethanols," Australian Journal of Chemistry 50:1091-1096 (1997).
Dorwald, F.Z. et al., "Side Reactions in Organic Synthesis," Wiley: VCH, Weinheim p. IX of Preface (2005).
Dorwald, F.Z. et al., "Side Reactions in Organic Synthesis," Wiley: VCH, Weinheim p. IX of Preface p. 1-15 (2005).

\* cited by examiner

Figure 1
[A]
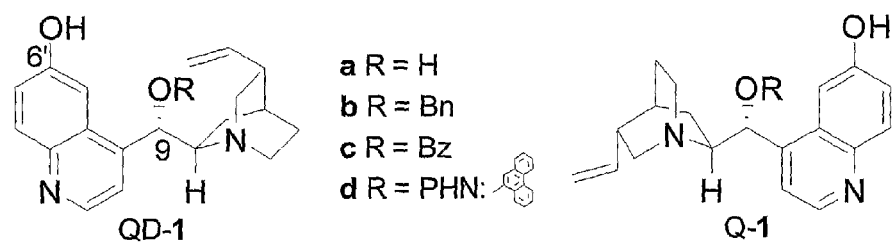
[B]
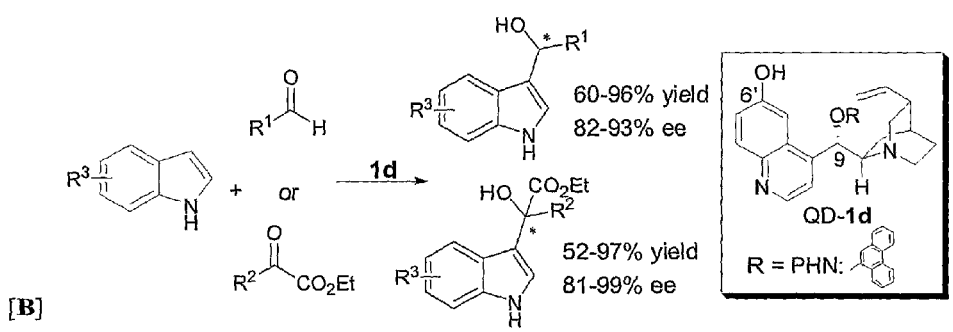

| cat. | T/ °C | t/ h | conv./%[a] | ee/%[b] |
|---|---|---|---|---|
| QD | 23 | 20 | 68% | -72% |
| CN | 23 | 20 | <10% | 7% |
| QD-1a | 23 | 20 | 82% | 83% |
| QD-1b | 23 | 20 | 54% | 88% |
| QD-1c | 23 | 20 | <10% | 85% |
| QD-1d | 23 | 20 | 74% | 89% |
| Q-1d | 23 | 20 | 78% | -87% |

[a]Determined by $^1$HNMR analysis; [b]Enantiomeric excess were determined by HPLC.

Figure 3

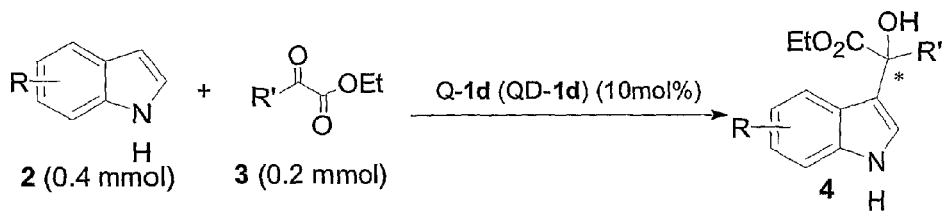

| entry | R | | R' | | T/°C | t/h | Yield/% [b] | ee/% [c] |
|---|---|---|---|---|---|---|---|---|
| 1 | H | 2A | But— | 3a | 23 | 63(62) | 89(96) | 87(88) |
| 2 | 6-MeO | 2B | But— | 3a | 23 | 40(40) | 86(79) | 84(88) |
| 3 | H | 2A | Ph— | 3b | 23 | 44(43) | 79(80) | 88(90) |
| 4 | H | 2A | 4-CN-Ph- | 3c | 23 | 56(55) | 88(77) | 97(97) |
| 5 | 4-MeO | 2C | 4-CN-Ph- | 3c | 23 | 64(64) | 79(79) | 99(99) |
| 6 | 5-Cl | 2D | 4-CN-Ph- | 3c | 23 | 71(70) | 85(96) | 96(94[g]) |
| 7 | 6-MeO | 2B | 4-CN-Ph- | 3c | 23 | 58(59) | 97(97) | 97(96) |
| 8 | 6-Br | 2E | 4-CN-Ph- | 3c | 23 | 61(61) | 67(80) | 95(95) |
| 9 | 7-Me | 2F | 4-CN-Ph- | 3c | 23 | 66(66) | 96(85) | 97(97) |
| 10 | H | 2A | 4-NO$_2$-Ph- | 3d | 23 | 72(71) | 88(95) | 98(95) |
| 11 | H | 2A | 4-Cl-Ph- | 3e | 23 | (24) | (13[f]) | (95) |
| 12[d] | H | 2A | 4-Cl-Ph- | 3e | 23 | (88) | (93) | (93) |
| 13[e] | H | 2A | 4-Cl-Ph- | 3e | 70 | 24(24) | 97(96) | 89(86) |
| 14[d] | H | 2A | Ph- | 3f | 23 | 88(88) | 63(71) | 94(93) |
| 15[e] | H | 2A | Ph- | 3f | 70 | 36(36) | 92(91) | 86(86) |
| 16[e] | 6-MeO | 2B | Ph- | 3f | 70 | 28(29) | 92(72) | 84(82) |
| 17[e] | 6-Cl | 2G | Ph- | 3f | 70 | 51(51) | 96(87) | 84(81) |
| 18[e] | H | 2A | 4-MeO-Ph- | 3g | 70 | 56 | 52 | 83 |

[a] Unless noted, reactions were carried with 0.2 mmol of 3, 0.4 mmol of 2 in 0.4 mL Et$_2$O with 10 mol% Q-1d, the results in parentheses were obtained with QD-1d to give opposite enantiomer, see Supporting Information for details; [b] Isolated yield; [c] Determined by HPLC analysis; [d] The reaction were carried out in ether (10 M); [e] The reaction were carried out in TBME(10 M); [f] Conversion was determined by $^1$HNMR analysis; [g] The absolute configuration was determined to be S, see Supporting Information for details.

| Entry | R | | R' | | T/°C | t/h | 6/7 [a] | yield/% [b] | ee/% [c] |
|---|---|---|---|---|---|---|---|---|---|
| 1 | H | 2A | EtO$_2$C- | 5a[d] | r.t. | 6 | >95/5 | 95(85) | 93(93) |
| 2 | 6-Br | 2E | EtO$_2$C- | 5a[d] | r.t. | 4 | >95/5 | 96(95) | 90(90) |
| 3 | 6-OMe | 2B | EtO$_2$C- | 5a[d] | r.t. | 4 | >95/5 | 94(93) | 90(82) |
| 4 | H | 2A | 2-NO$_2$-Ph- | 5b | r.t. | 72 | >95/5 | 96(95) | 90(89) |
| 5 | H | 2A | 4-NO$_2$-Ph- | 5c | r.t. | 72 | >95/5 | 90(90) | 88(83) |
| 6 | H | 2A | 4-CF$_3$-Ph- | 5d | r.t. | 72 | >95/5 | 85(83) | 88(88) |
| 7 | H | 2A | 4-Cl-Ph- | 5e | 70 | 40 | 7/1 | 75 | 83 |
| 8 | H | 2A | Ph- | 5f | 70 | 48 | 2/1 | 60 | 82 |

[a] The ratio was determined by $^1$HNMR analysis of crude product; [b] Isolated yield; [c] Determined by HPLC analysis; [d] ~50 wt% in toluene.

Figure 8
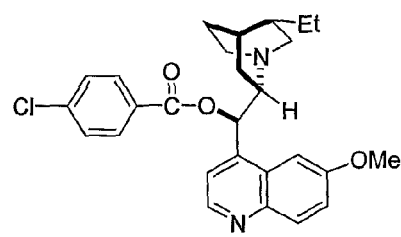
DHQ-CLB
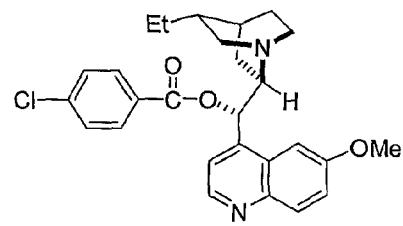
DHQD-CLB
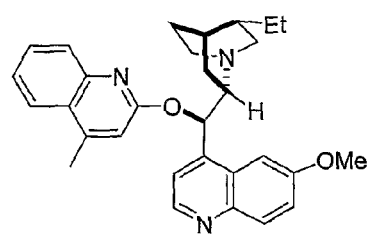
DHQ-MEQ
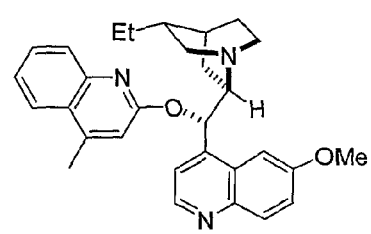
DHQD-MEQ
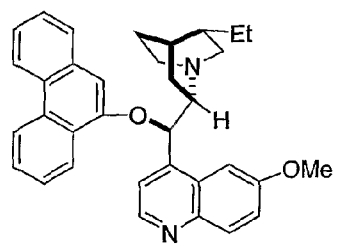
DHQ-AQN
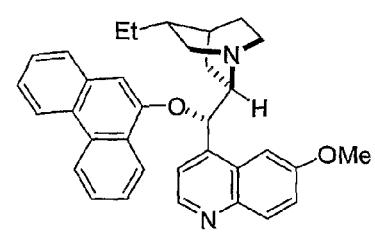
DHQD-AQN
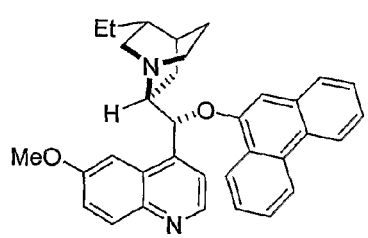
DHQ-PHN
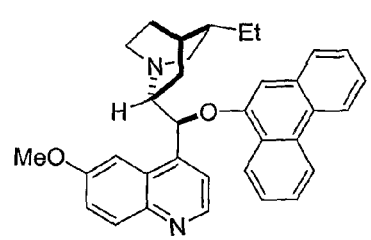
DHQD-PHN

ASYMMETRIC FRIEDEL-CRAFTS ALKYLATIONS CATALYZED BY BIFUNCTIONAL CINCHONA ALKALOIDS

GOVERNMENT SUPPORT

The invention was made with support provided by the National Institutes of Health (GM-61591); therefore, the government has certain rights in the invention.

RELATED APPLICATIONS

This application claims priority to PCT Application No. PCT/US06/045960, filed Dec. 1, 2006, which claims the benefit of the filing date of U.S. Provisional Patent Application Ser. No. 60/742,102, filed Dec. 2, 2005; and U.S. Provisional Patent Application Ser. No. 60/781,624, filed Mar. 13, 2006.

BACKGROUND OF THE INVENTION

Methods for the preparation and functionalization of indoles are important due to the frequent appearance of indoles in biologically interesting natural and unnatural compounds. Sundberg, R. J. *Indoles*; Academic Press: London, 1996; Saxton, J. E. *Nat. Prod. Rep.* 1997, 559; Borschberg, H.-J. *Curr. Org. Chem.* 2005, 9, 1465; Kleeman, A.; Engel, J.; Kutscher, B.; Reichert, D. *Pharmaceutical Substances*, 4th ed.; Thieme: New York, 2001; "Friedel-Crafts Alkylation": Olah, G. A.; Krishnamurty, R.; Prakash, G. K. S. in *Comprehensive Organic Synthesis, Vol. III* (Eds.: B. M. Trost, I. Fleming), Pergamon, Oxford, 1st ed., 1991, p. 293; Roberts, R. M. A.; Khalaf, A. *Friedel-Crafts Alkylation Chemistry A Century of Discovery*, Marcel Dekker, New York, 1984; Olah, G. A. *Friedel-Crafts and Related Reactions, Vol. II*, part 1, Wiley-Interscience, New York, 1964; and Cacchi, S.; Fabrizi, G. *Chem. Rev.* 2005, 105, 2873.

The development of catalytic enantioselective methods for the facile synthesis of optically active indole derivatives has recently attracted significant attention. The electron-rich nature of the indole ring renders enantioselective Friedel-Crafts reactions of indoles with readily available prochiral electrophilic starting materials a strategically important approach to access enantiomerically enriched indole derivatives. For reviews, see: Jørgensen, K. A. *Synthesis* 2003, 1117; b) Bandini, M.; Melloni, A.; Umani-Ronchi, A. *Angew. Chem. Int. Ed.* 2004, 43, 550. For recent examples of catalytic enatioselective synthesis of indole derivatives, see: a) Bandini, M.; Melloni, A.; Piccinelli, F.; Sinisi, R.; Tommasi, S.; Umani-Ronchi, A. *J. Am. Chem. Soc.* 2006, 128, 1424; b) Davies, H. M. L.; Manning, J. R. *J. Am. Chem. Soc.* 2006, 128, 1060; c) Seayad, J.; Seayad, A. M.; List, B. *J. Am. Chem. Soc.* 2006, 128, 1086; d) Taylor, M. S.; Jacobsen, E. N. *J. Am. Chem. Soc.* 2004, 126, 10558. For catalytic asymmetric Michael additions of indoles catalyzed by chiral Lewis acids, see: a) Jensen, K. B.; Thorhauge, J.; Hazell, R. G.; Jørgensen, K. A. *Angew. Chem. Int. Ed.* 2001, 40, 160; b) Zhou, J.; Tang, Y. *J. Am. Chem. Soc.* 2002, 124, 9030; c) Bandini, M.; Fagioli, M.; Melchiorre, P.; Melloni, A.; Umani-Ronchi, A. *Tetrahedron Lett.* 2003, 44, 5846; d) Evans, D. A.; Scheidt, K. A.; Fandrick, K. R.; Lam, H. W.; Wu, J. *J. Am. Chem. Soc.* 2003, 125, 10780; e) Evans, D. A.; Fandrick, K. R.; Song, H.-J. *J. Am. Chem. Soc.* 2005, 127, 8942; f) Palomo, C.; Oiarbide, M.; Kardak, B. G.; Garcia, J. M.; Linden, A. *J. Am. Chem. Soc.* 2005, 127, 4154 g) Jia, Y.-X., Zhu, S.-F.; Yang, Y.; Zhou, Q.-L. *J. Org. Chem.* 2006, 71, 75; h) Yamazaki, S.; Iwata, Y. *J. Org. Chem.* 2006, 71, 739; for resolution of epoxides with indole see: i) Bandini, M.; Cozzi, P.; Melchiorre, G. P.; Umani-Ronchi, A. *Angew. Chem. Int. Ed.* 2004, 43, 84. For catalytic asymmetric Michael additions of indoles catalyzed by organic catalyst, see: a) Paras, N. A.; MacMillan, D. W. C. *J. Am. Chem. Soc.* 2001, 123, 4370; b) Austin, J. F.; MacMillan, D. W. C. *J. Am. Chem. Soc.* 2002, 124, 1172; c) Paras, N. A.; MacMillan, D. W. C. *J. Am. Chem. Soc.* 2002, 124, 7824; d) Huang, Y.; Walji, A. M.; Larsen, C. H.; MacMillan, D. W. C. *J. Am. Chem. Soc.* 2005, 127, 15051; e) Zhuang, W.; Hazell, R. G.; Jørgensen, K. A. *Org. Biomol. Chem.* 2005, 3, 2566; f) Herrera, R. P.; Sgarzani, V.; Bernardi, L.; Ricci, A. *Angew. Chem. Int. Ed.* 2005, 44, 6576. For catalytic asymmetric addition of indoles to ethyl 3,3,3-trifluoropyruvate, see: a) Zhuang, W.; Gathergood, N.; Hazell, R. G.; Jorgensen, K. A. *J. Org. Chem.* 2001, 66, 1009; b) Török, B.; Abid, M.; London, G.; Esquibel, J.; Török, M. S.; Mhadgut, C.; Yan, P.; Prakash, G. K. S. *Angew. Chem. Int. Ed.* 2005, 44, 3086. For catalytic asymmetric Friedel-Crafts additions of indoles to imines, see: Johannsen, M. *Chem. Comm.* 1999, 2233.

Several enantioselective conjugate additions of indoles to Michael acceptors have been developed using either chiral metallic or organic catalysts. These studies established considerable substrate scope with respect to both the indoles and the Michael acceptors. In contrast, a catalytic enantioselective 1,2-nucleophilic addition that is broadly applicable to both indoles and carbonyl compounds is lacking, although such a reaction would represent another direct and versatile means to synthesize enantiomerically enriched chiral indole derivatives. While high enantioselectivity has been achieved with both chiral metal and organic catalysts, these catalysts are only effective with ethyl 3,3,3-trifluoropyruvate as the electrophile.

In a recent report of the cinchonine- or cinchonidine-catalzyed addition of indoles to ethyl 3,3,3-trifluoropyruvate, Török, Prakash and coworkers demonstrated that blocking either the quinuclidine or the 9-OH led to dramatically reduced enantioselectivity with the natural cinchona alkaloids. Török, B.; Abid, M.; London, G.; Esquibel, J.; Török, M. S.; Mhadgut, C.; Yan, P.; Prakash, G. K. S. *Angew. Chem. Int. Ed.* 2005, 44, 3086. Thus, cinchonine was postulated to function as a base-acid bifunctional catalyst to activate simultaneously the indole and ethyl 3,3,3-trifluoropyruvate via the quinuclidine and the 9-OH moiety, respectively, to achieve synthetic useful enantioselectivity.

In addition, synthetic and mechanistic studies have established that cooperative hydrogen-bonding catalysis with 6'-OH cinchona alkaloids as base-acid bifunctional catalysts can provide a useful platform for the development of highly enantioselective conjugate additions and nitroaldol (Henry) reaction. Li, H.; Wang, Y.; Tang, L.; Deng, L. *J. Am. Chem. Soc.* 2004, 126, 9906-9907; Li, H.; Wang, Y.; Tang, L.; Wu, F.; Liu, X.; Guo, C.; Foxman, B. M.; Deng, L. *Angew. Chem. Int. Ed.* 2005, 44, 105-108; Liu, X.; Li, H.; Deng, L. *Org. Lett.* 2005, 7, 167-169; Li, H.; Song, J.; Liu, X.; Deng, L. *J. Am. Chem. Soc.* 2005, 127, 8948-8949; Li, H.; Wang, B.; Deng, L. *J. Am. Chem. Soc.* 2006, 128, 732; and Wu, F.; Li, H.; Hong, R.; Deng, L. *Angew. Chem. Int. Ed.* 2006, 45, 947. While the high efficiency of 6'-OH cinchona alkaloids in the promotion of mechanistically unrelated C—C bond formations had been demonstrated, it was unknown if the 6'-OH cinchona alkaloids might function as efficient catalysts for enantioselective Friedel-Crafts reactions of indoles with carbonyl compounds. In particular, whether the more acidic 6'-phenol (relative to the C9-alcohol) could be used to achieve effective activation of a broad range of carbonyls for the enantioselective Friedel-Crafts reaction with indoles. Remarkably, we have discovered that cinchona alkaloids can be used to achieve effective activation of a broad range of carbonyls for the asymmetric Friedel-Crafts reaction.

SUMMARY

In certain embodiments, the present invention relates to methods for asymmetric Friedel-Crafts alkylation catalyzed by bifunctional cinchona alkaloids. In certain embodiments, the catalyst is a 6'-OH cinchona alkaloid. In certain embodiments, the electrophile is an α-ketoester or aldehyde. In certain embodiments, the nucleophile is an aromatic heterocycle. In certain embodiments, the nucleophile is an aromatic N-containing heterocycle. In certain embodiments, the nucleophile is an indole. In certain embodiments, the methods of the invention are relatively insensitive to concentration, temperature, air and moisture.

BRIEF DESCRIPTION OF THE FIGURES

FIG. 1 depicts [A] selected 6'-OH cinchona alkaloid derivatives and [B] generalized enantioselective Friedel-Crafts reactions with representative yields and enantiomeric excesses.

FIG. 2 depicts asymmeteric Friedel-Crafts reactions of indole 2A with α-ketoester 3a.

FIG. 3 depicts highly enantioselective Friedel-Crafts additions of indoles (2) to α-ketoesters (3) promoted by Q-1d or QD-1d (in parentheses).

FIG. 8 depicts the structures of certain catalysts used in the methods of the present invention, and the abbreviations used herein for them.

DETAILED DESCRIPTION OF THE INVENTION

In certain embodiments, the present invention relates to methods for asymmetric Friedel-Crafts alkylation catalyzed by bifunctional cinchona alkaloids. In certain embodiments, the catalyst is a 6'-OH cinchona alkaloid. In certain embodiments, the electrophile is an α-ketoester or aldehyde. In certain embodiments, the nucleophile is an aromatic heterocycle. In certain embodiments, the nucleophile is an aromatic N-containing heterocycle. In certain embodiments, the nucleophile is an indole. In certain embodiments, the methods of the invention are relatively insensitive to concentration, temperature, air and moisture.

Figure 2:
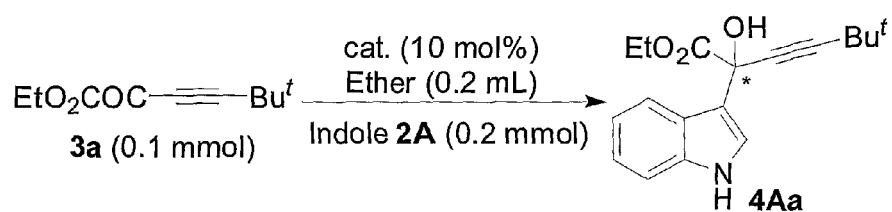

FIG. 2 shows the results of cinchona alkaloid-catalyzed reaction of indole (2A) with an alkynyl α-ketoester 3a. Specifically, 6'-OH cinchcona alkaloids 1 were found to afford better activity and enantioselectivity than provided by quinidine or cinchonine, and the highest enantioselectivity was obtained with QD-1d. Importantly, a complete reaction could be accomplished with QD-1d to produce the corresponding Friedel-Crafts adduct in 96% yield and 88% ee (entry 1, FIG. 3).

Further studies revealed that catalyst 1d tolerates structural variation in the indoles and the alkynyl α-ketoesters (entries 1-3, FIG. 3). Moreover, the scope of the reaction could be readily extended to aryl α-ketoesters (entries 4-17, FIG. 3). With aryl α-keto esters bearing a strong electron-withdrawing substituent, the enantio selectivity could be sustained at a very high level for additions of a wide variety of indoles substituted with electron-donating or electron-withdrawing groups at 4-7 positions (entries 4-10, FIG. 3). As expected aryl α-ketoesters bearing a less electron-withdrawing group such as ketoester 3e are less reactive (entry 11, FIG. 3). It was found, however, that the enantioselectivity of 1d is insensitive to reaction concentration. Consequently, by carrying out the 1d-catalyzed reaction at 10.0 M concentration, 3e could be converted into the desired product in high yield and excellent enantioselectivity (entry 12, FIG. 3). The enantioselectivity of the reaction remained high even when the reaction was performed at 10.0 M and 70° C. (entry 18, FIG. 3).

Figure 4:
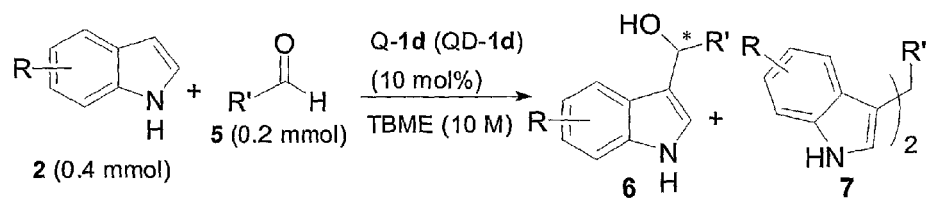
FIG. 4 depicts asymmeteric Friedel-Crafts additions of indoles (2) to aldehydes (5) promoted by Q-1d or QD-1d (in parentheses).

Catalyst 1d was also found to be effective for Friedel-Crafts reactions of indoles with aldehydes (FIG. 4). Reactions with glyoxalate 5a proceeded most rapidly and afforded the best enantioselectivity (entries 1-3, FIG. 4). The addition of indole to various simple aromatic aldehydes proceeded in good enantioselectivity and useful yield (entries 4-8, FIG. 4). These results provide the first demonstration of a highly enantioselective catalytic Friedel-Crafts reaction with a simple aldehyde. For Friedel-Crafts addition of indoles to aldehydes to form bis-indole adducts, see: a) Chakrabarty, M.; Mukherji, A.; Karmakar, S.; Arima, S.; Harigaya, Y. *Heterocycles* 2006, 68, 331; b) Nair, V.; Abhilash, K. G.; Vidya, N. *Org. Lett.* 2005, 5857; c) Gibbs, T. J. K.; Tomkinson, N. C. O. *Org. Biomol. Chem.* 2005, 3, 4043.

DEFINITIONS

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents, such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g., tosylates), chlorides, bromides, iodides, and the like.

The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "Bronsted base" is art-recognized and refers to an uncharged or charged atom or molecule, e.g., an oxide, amine, alkoxide, or carbonate, that is a proton acceptor.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an ee for a particular enantiomer that is larger than the ee of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from about 0.001 to about 50 mole percent, still more preferably from about 0.01 to about 10 mole percent, and even more preferably from about 0.1 to about 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\% \text{ Enantiomeric Excess } A(ee) = (\% \text{ Enantiomer } A) - (\% \text{ Enantiomer } B)$$

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than about 20%, more preferably greater than about 50%, even more preferably greater than about 70%, and most preferably greater than about 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least about 75%. "Substantially non-racemic" refers to preparations of the catalyst which have greater than about 90% ee for a given enantiomer of the catalyst, more preferably greater than about 95% ee.

The term "heteroatom" is art-recognized and refers to an atom of any element other than carbon or hydrogen. Illustrative heteroatoms include boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The term "perfluoroalkyl" is art-recognized and refers to an alkyl group in which all the hydrogen atoms have been replaced with fluorine atoms. For example, trifluoromethyl and pentafluoroethyl are examples of perfluoroalkyl groups.

The terms "alkenyl" and "alkynyl" refer to unsaturated aliphatic groups analogous in length and possible substitution to the alkyls described above, but which contain at least one double or triple carbon-carbon bond, respectively.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and includes to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloakyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that may be represented by the general formulas:

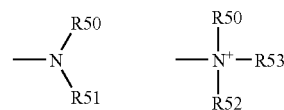

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

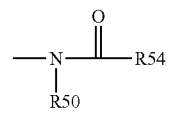

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

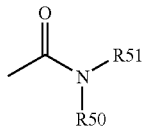

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

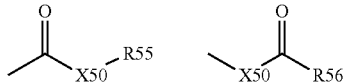

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

As used herein, "alkyloyl" means —C(=O)-alkyl. As used herein, "aryloyl" means —C(=O)-aryl. As used herein, "arylalkyloyl" means —C(=O)-alkyl-aryl. As used herein, "heteroaryloyl" means —C(=O)-heteroaryl. As used herein, "heteroarylalkyloyl" means —C(=O)-alkyl-heteroaryl.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

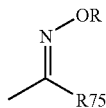

wherein R75 is hydrogen, alkyl, cycloalkyl, alkenyl, alkynyl, aryl, aralkyl, or —(CH$_2$)$_m$—R6t. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

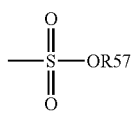

in which R57 is an electron pair, hydrogen, alkyl, cycloalkyl, or aryl.

The term "sulfate" is art recognized and includes a moiety that may be represented by the general formula:

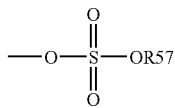

in which R57 is as defined above.

The term "sulfonamido" is art recognized and includes a moiety that may be represented by the general formula:

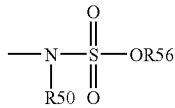

in which R50 and R56 are as defined above.

The term "sulfamoyl" is art-recognized and refers to a moiety that may be represented by the general formula:

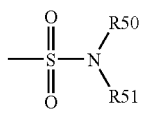

in which R50 and R51 are as defined above.

The term "sulfonyl" is art-recognized and refers to a moiety that may be represented by the general formula:

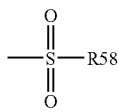

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

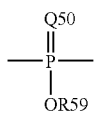

wherein Q50 represents S or O, and R59 represents hydrogen, a lower alkyl or an aryl. When used to substitute, e.g., an alkyl, the phosphoryl group of the phosphorylalkyl may be represented by the general formulas:

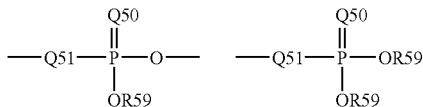

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

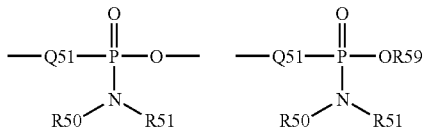

wherein Q51, R50, R51 and R59 are as defined above.

The term "phosphonamidite" is art-recognized and may be represented in the general formulas:

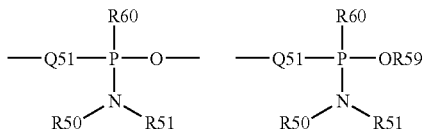

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

Catalysts of the Invention

The catalysts employed in the subject methods are non-racemic chiral amines which present an asymmetric environment, causing stereochemical discrimination between two stereogenic faces of a carbonyl-containing compound; or two or more prochiral moieties (e.g., related by symmetry in a prochiral or meso molecule (i.e., a molecule comprising at least two chiral centers), both of which comprise an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity.

As mentioned above, the choice of catalyst substituents can also effect the electronic properties of the catalyst. Substitution of the catalyst with electron-rich (electron-donating) moieties (for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

In certain embodiments, the catalyst has a molecular weight less than 2,000 g/mol, less than 1,000 g/mol, or less than 500 g/mol. Additionally, the substituents on the catalyst can be selected to influence the solubility of the catalyst in a particular solvent system.

In certain embodiments, the chiral, non-racemic tertiary amine catalyst comprises a 1-azabicyclo[2.2.2]octane moiety or a 1,4-diazabicyclo[2.2.2]octane moiety.

In certain embodiments, the chiral, non-racemic tertiary amine catalyst is a cinchona alkaloid, (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, or DHQD-PHN.

One aspect of the present invention relates to a chiral, non-racemic tertiary amine compound represented by formula I:

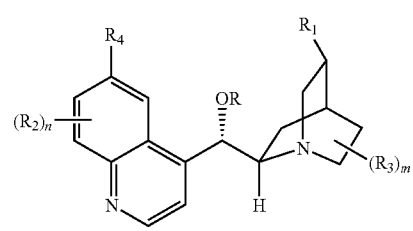

wherein, independently for each occurrence:

R represents hydrogen, alkyl, aryl, heteroaryl, aralkyl, heteroaralkyl, alkyloyl, aryloyl, arylalkyloyl, heteroaryloyl, or heteroarylalkyloyl;

R$_1$ represents alkyl, or alkenyl;

R$_2$ and R$_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive;

R$_4$ represents —OH, —SH, or —NHR$_5$; and

R$_5$ represents hydrogen, acyl or aralkyl.

In certain embodiments, the compounds of the present invention are represented by formula I and any of the attendant definitions, wherein R$_4$ represents OH.

In certain embodiments, the compounds of the present invention are represented by formula I and any of the attendant definitions, wherein R$_4$ represents OH; and R represents hydrogen, aryl, aralkyl, or aryloyl.

In certain embodiments, the compounds of the present invention are represented by formula I and any of the attendant definitions, wherein R$_4$ represents OH; and R represents —H,

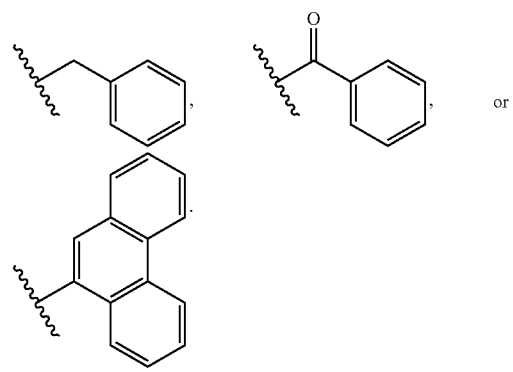

In certain embodiments, the compounds of the present invention are represented by formula I and any of the attendant definitions, wherein $R_4$ represents OH; and R represents

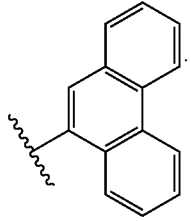 [SMILES: *c1cc2ccccc2c2ccccc12]

In certain embodiments, the compounds of the present invention are represented by formula I and any of the attendant definitions, wherein $R_4$ represents OH; and $R_1$ is alkyl.

In certain embodiments, the compounds of the present invention are represented by formula I and any of the attendant definitions, wherein $R_4$ represents OH; and $R_1$ is ethyl.

In certain embodiments, the compounds of the present invention are represented by formula I and any of the attendant definitions, wherein $R_4$ represents OH; and $R_1$ is alkenyl.

In certain embodiments, the compounds of the present invention are represented by formula I and any of the attendant definitions, wherein $R_4$ represents OH; and $R_1$ is —CH=CH$_2$.

In certain embodiments, the compounds of the present invention are represented by formula I and any of the attendant definitions, wherein $R_4$ represents OH; and n is 0.

In certain embodiments, the compounds of the present invention are represented by formula I and any of the attendant definitions, wherein $R_4$ represents OH; and m is 0.

In certain embodiments, the compounds of the present invention are represented by formula I and any of the attendant definitions, wherein $R_4$ represents OH; R is aryl and $R_1$ is ethyl.

In certain embodiments, the compounds of the present invention are represented by formula I and any of the attendant definitions, wherein $R_4$ represents OH; R is

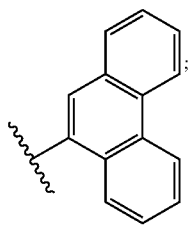 [SMILES: *c1cc2ccccc2c2ccccc12]

and $R_1$ is ethyl.

In certain embodiments, the compounds of the present invention are represented by formula I and any of the attendant definitions, wherein $R_4$ represents OH; R is aryl; and $R_1$ is —CH=CH$_2$.

In certain embodiments, the compounds of the present invention are represented by formula I and any of the attendant definitions, wherein $R_4$ represents OH; R is

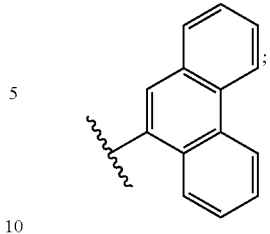

and $R_1$ is —CH=CH$_2$.

In certain embodiments, the compounds of the present invention are represented by formula I and any of the attendant definitions, wherein $R_4$ represents OH; R is aryl; $R_1$ is ethyl; m is 0; and n is 0.

In certain embodiments, the compounds of the present invention are represented by formula I and any of the attendant definitions, wherein $R_4$ represents OH; R is

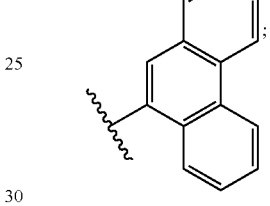

$R_1$ is ethyl; m is 0; and n is 0.

In certain embodiments, the compounds of the present invention are represented by formula I and any of the attendant definitions, wherein $R_4$ represents OH; R is aryl; $R_1$ is —CH=CH$_2$; m is 0; and n is 0.

In certain embodiments, the compounds of the present invention are represented by formula I and any of the attendant definitions, wherein $R_4$ represents OH; R is

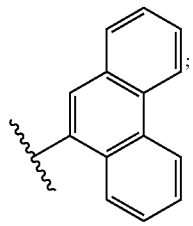 [SMILES: *c1cc2ccccc2c2ccccc12]

$R_1$ is —CH=CH$_2$; m is 0; and n is 0.

Another aspect of the present invention relates to a chiral, non-racemic tertiary amine compound represented by formula II:

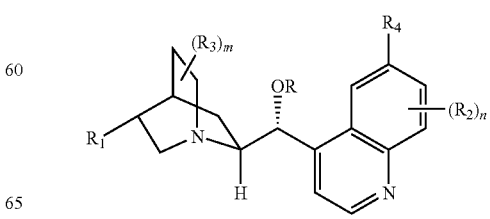

wherein, independently for each occurrence:
R represents hydrogen, alkyl, aryl, heteroaryl, aralkyl, heteroaralkyl, alkyloyl, aryloyl, arylalkyloyl, heteroaryloyl, or heteroarylalkyloyl;
$R_1$ represents alkyl, or alkenyl;
$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;
n is an integer from 0 to 5 inclusive;
m is an integer from 0 to 8 inclusive;
$R_4$ represents —OH, —SH, or —NHR$_5$; and
$R_5$ represents hydrogen, acyl or aralkyl.

In certain embodiments, the compounds of the present invention are represented by formula II and any of the attendant definitions, wherein $R_4$ represents OH.

In certain embodiments, the compounds of the present invention are represented by formula II and any of the attendant definitions, wherein $R_4$ represents OH; and R represents hydrogen, aryl, aralkyl, or aryloyl.

In certain embodiments, the compounds of the present invention are represented by formula II and any of the attendant definitions, wherein $R_4$ represents OH; and R represents —H,

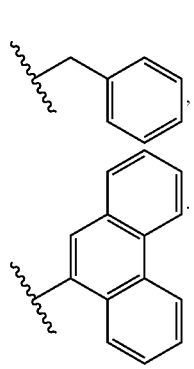

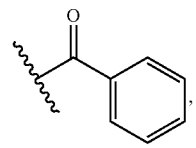 , or

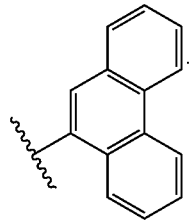 [SMILES: *c1cc2ccccc2c2ccccc12]

In certain embodiments, the compounds of the present invention are represented by formula II and any of the attendant definitions, wherein $R_4$ represents OH; and R represents

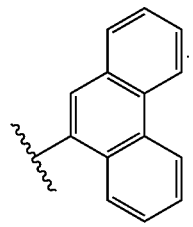 [SMILES: *c1cc2ccccc2c2ccccc12]

In certain embodiments, the compounds of the present invention are represented by formula II and any of the attendant definitions, wherein $R_4$ represents OH; and $R_1$ is alkyl.

In certain embodiments, the compounds of the present invention are represented by formula II and any of the attendant definitions, wherein $R_4$ represents OH; and $R_1$ is ethyl.

In certain embodiments, the compounds of the present invention are represented by formula II and any of the attendant definitions, wherein $R_4$ represents OH; and $R_1$ is alkenyl.

In certain embodiments, the compounds of the present invention are represented by formula II and any of the attendant definitions, wherein $R_4$ represents OH; and $R_1$ is —CH=CH$_2$.

In certain embodiments, the compounds of the present invention are represented by formula II and any of the attendant definitions, wherein $R_4$ represents OH; and n is 0.

In certain embodiments, the compounds of the present invention are represented by formula II and any of the attendant definitions, wherein $R_4$ represents OH; and m is 0.

In certain embodiments, the compounds of the present invention are represented by formula II and any of the attendant definitions, wherein $R_4$ represents OH; R is aryl; and R is ethyl.

In certain embodiments, the compounds of the present invention are represented by formula II and any of the attendant definitions, wherein $R_4$ represents OH; R is

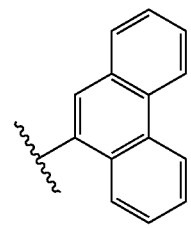 [SMILES: *c1cc2ccccc2c2ccccc12]

and $R_1$ is ethyl.

In certain embodiments, the compounds of the present invention are represented by formula II and any of the attendant definitions, wherein $R_4$ represents OH; R is aryl; and $R_1$ is —CH=CH$_2$.

In certain embodiments, the compounds of the present invention are represented by formula II and any of the attendant definitions, wherein $R_4$ represents OH; R is

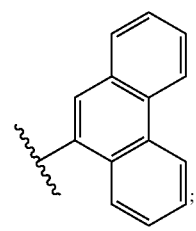 [SMILES: *c1cc2ccccc2c2ccccc12]

and $R_1$ is —CH=CH$_2$.

In certain embodiments, the compounds of the present invention are represented by formula II and any of the attendant definitions, wherein $R_4$ represents OH; R is aryl; $R_1$ is ethyl; m is 0; and n is 0.

In certain embodiments, the compounds of the present invention are represented by formula II and any of the attendant definitions, wherein $R_4$ represents OH; R is

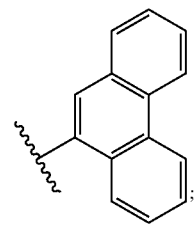 [SMILES: *c1cc2ccccc2c2ccccc12]

$R_1$ is ethyl; m is 0; and n is 0.

In certain embodiments, the compounds of the present invention are represented by formula II and any of the attendant definitions, wherein R is aryl; R1 is —CH=CH₂; m is 0; and n is 0.

In certain embodiments, the compounds of the present invention are represented by formula II and any of the attendant definitions, wherein R₄ represents OH; R is

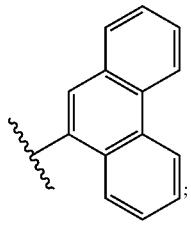 [SMILES: *c1cc2ccccc2c2ccccc12]

R₁ is —CH=CH₂; m is 0; and n is 0.

Methods of the Invention—Catalyzed Asymmetric Friedel-Crafts Reactions

One aspect of the present invention relates to a process for stereoselectively producing compounds with at least one stereogenic center from prochiral, meso, or racemic starting materials. An advantage of this invention is that enantiomerically enriched products can be synthesized from prochiral, meso, or racemic reactants. Another advantage is that yield losses associated with the production of an undesired stereoisomer can be substantially reduced or eliminated altogether.

In general, the invention features a stereoselective addition process which comprises combining a nucleophilic reactant, a prochiral or chiral substrate, and at least a catalytic amount of non-racemic chiral catalyst of particular characteristics (as described herein). Suitable substrates for the reaction include prochiral aldehydes and prochiral ketones susceptible to attack by the nucleophile. The combination of substrate, nucleophile, and catalyst is maintained under conditions appropriate for the chiral catalyst to catalyze the addition of the nucleophilic reactant to the prochiral aldehyde or prochiral ketone. This reaction can be applied to enantioselective processes as well as diastereoselective processes. It may also be adapted for kinetic resolutions, dynamic kinetic resolutions, and regioselective reactions which may be catalyzed according to the present invention.

Moreover, the methods of the invention can provide optically active products with very high stereoselectivity (e.g., enantioselectivity or diastereoselectivity) or regioselectivity. In certain embodiments, the methods yield products with an enantiomeric excess or diastereomeric excess of greater than about 50%, greater than about 70%, greater than about 90%, or greater than about 95%. The methods of this invention can also be carried out under reaction conditions suitable for commercial use, and typically proceed at reaction rates suitable for large scale operations.

The chiral products produced by the asymmetric synthesis processes of this invention can undergo further reaction(s) to afford desired derivatives thereof. Such permissible derivatization reactions can be carried out in accordance with conventional procedures known in the art. The invention expressly contemplates the preparation of end-products and synthetic intermediates which are useful for the preparation or development or both of therapeutic compounds.

One aspect of the present invention relates to a method of preparing a chiral, non-racemic alcohol from a prochiral aldehyde or prochiral ketone, comprising the step of:

reacting a prochiral aldehyde or prochiral ketone with an aromatic compound in the presence of a catalyst; thereby producing a chiral, non-racemic alcohol; wherein said catalyst is Q-PP, Q-TB, QD-PP, QD-TB, (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN or DHQD-PHN.

Another aspect of the present invention relates to a method of preparing a chiral, non-racemic alcohol from a prochiral aldehyde or prochiral ketone, comprising the step of:

reacting a prochiral aldehyde or prochiral ketone with an aromatic compound in the presence of a catalyst; thereby producing a chiral, non-racemic alcohol; wherein said catalyst is represented by formula I:

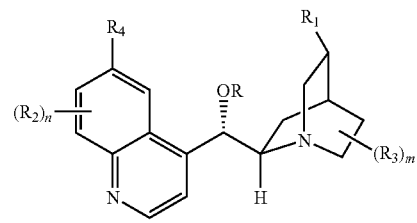

wherein, independently for each occurrence:

R represents hydrogen, alkyl, aryl, heteroaryl, aralkyl, heteroaralkyl, alkyloyl, aryloyl, arylalkyloyl, heteroaryloyl, or heteroarylalkyloyl;

R₁, represents alkyl, or alkenyl;

R₂ and R₃ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive;

R₄ represents —OH, —SH, or —NHR₅; and

R₅ represents hydrogen, acyl or aralkyl.

In certain embodiments, the present invention relates to the aforementioned method and any of the attendant definitions, wherein R₄ represents OH.

In certain embodiments, the present invention relates to the aforementioned method and any of the attendant definitions, wherein R₄ represents OH; and R represents hydrogen, aryl, aralkyl, or aryloyl.

In certain embodiments, the present invention relates to the aforementioned method and any of the attendant definitions, wherein R₄ represents OH; and R represents —H,

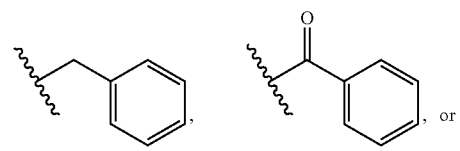

-continued

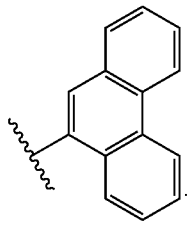 [SMILES: *c1cc2ccccc2c2ccccc12]

In certain embodiments, the present invention relates to the aforementioned method and any of the attendant definitions, wherein $R_4$ represents OH; and R represents

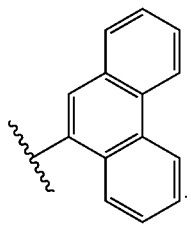 [SMILES: *c1cc2ccccc2c2ccccc12]

In certain embodiments, the present invention relates to the aforementioned method and any of the attendant definitions, wherein $R_4$ represents OH; and $R_1$ is alkyl.

In certain embodiments, the present invention relates to the aforementioned method and any of the attendant definitions, wherein $R_4$ represents OH; and $R_1$ is ethyl.

In certain embodiments, the present invention relates to the aforementioned method and any of the attendant definitions, wherein $R_4$ represents OH; and $R_1$ is alkenyl.

In certain embodiments, the present invention relates to the aforementioned method and any of the attendant definitions, wherein $R_4$ represents OH; and $R_1$ is —CH=CH$_2$.

In certain embodiments, the present invention relates to the aforementioned method and any of the attendant definitions, wherein $R_4$ represents OH; and n is 0.

In certain embodiments, the present invention relates to the aforementioned method and any of the attendant definitions, wherein $R_4$ represents OH; and m is 0.

In certain embodiments, the present invention relates to the aforementioned method and any of the attendant definitions, wherein $R_4$ represents OH; R is aryl and $R_1$ is ethyl.

In certain embodiments, the present invention relates to the aforementioned method and any of the attendant definitions, wherein $R_4$ represents OH; R is

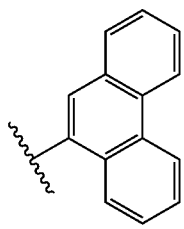

and $R_1$ is ethyl.

In certain embodiments, the present invention relates to the aforementioned method and any of the attendant definitions, wherein $R_4$ represents OH; R is aryl; and $R_1$ is —CH=CH$_2$.

In certain embodiments, the present invention relates to the aforementioned method and any of the attendant definitions, wherein $R_4$ represents OH; R is

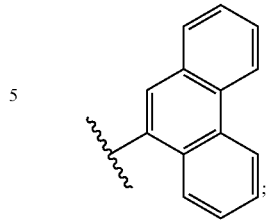

and $R_1$ is —CH=CH$_2$.

In certain embodiments, the present invention relates to the aforementioned method and any of the attendant definitions, wherein $R_4$ represents OH; R is aryl; $R_1$ is ethyl; m is 0; and n is 0.

In certain embodiments, the present invention relates to the aforementioned method and any of the attendant definitions, wherein $R_4$ represents OH; R is

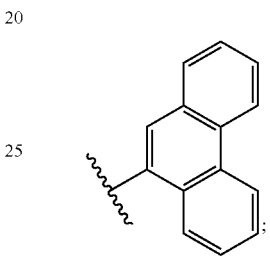

$R_1$ is ethyl; m is 0; and n is 0.

In certain embodiments, the present invention relates to the aforementioned method and any of the attendant definitions, wherein R4 represents OH; R is aryl; $R_1$ is —CH=CH$_2$; m is 0; and n is 0.

In certain embodiments, the present invention relates to the aforementioned method and any of the attendant definitions, wherein $R_4$ represents OH; R is

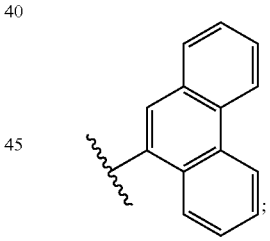

$R_1$ is —CH=CH$_2$; m is 0; and n is 0.

In certain embodiments, the present invention relates to the aforementioned method and any of the attendant definitions, wherein said prochiral aldehyde or prochiral ketone is represented by III:

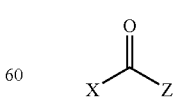

III wherein
X represents alkyl, aryl, heteroaryl, aralkyl, or heteroaralkyl; and
Z represents H, perfluoroalkyl, alkyl, aryl, heteroaryl, aralkyl, or heteroaralkyl.

In certain embodiments, the present invention relates to the aforementioned method and any of the attendant definitions, wherein said prochiral aldehyde or prochiral ketone is represented by III; and Z is H.

In certain embodiments, the present invention relates to the aforementioned method and any of the attendant definitions, wherein said prochiral aldehyde or prochiral ketone is represented by III; and X is aryl.

In certain embodiments, the present invention relates to the aforementioned method and any of the attendant definitions, wherein said prochiral aldehyde or prochiral ketone is represented by III; and X is a substituted or unsubstituted 6-membered single-ring aromatic group that may include from zero to four heteroatoms.

In certain embodiments, the present invention relates to the aforementioned method and any of the attendant definitions, wherein said prochiral aldehyde or prochiral ketone is represented by III; and X is a substituted or unsubstituted phenyl.

In certain embodiments, the present invention relates to the aforementioned method and any of the attendant definitions, wherein said prochiral aldehyde or prochiral ketone is represented by III; and X is

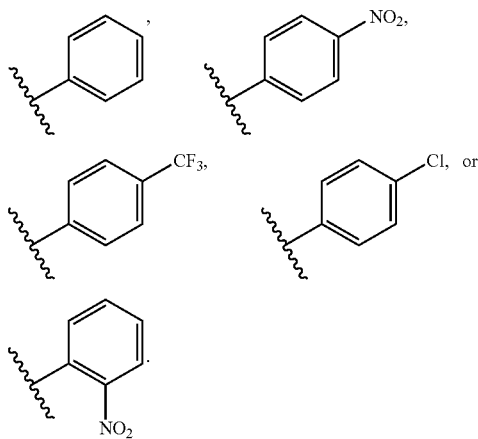

In certain embodiments, the present invention relates to the aforementioned method and any of the attendant definitions, wherein said prochiral aldehyde or prochiral ketone is represented by III; Z is H; and X is aryl.

In certain embodiments, the present invention relates to the aforementioned method and any of the attendant definitions, wherein said prochiral aldehyde or prochiral ketone is represented by III; Z is H; and X is

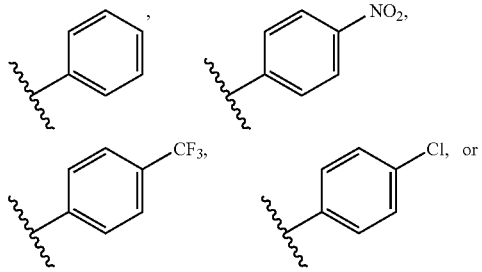

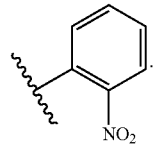

In certain embodiments, the present invention relates to the aforementioned method and any of the attendant definitions, wherein said prochiral aldehyde or prochiral ketone is represented by IV:

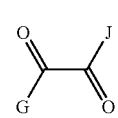

IV wherein

G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;

J represents H, perfluoroalkyl, alkyl, aryl, heteroaryl, aralkyl, or heteroaralkyl; and G and J may be connected by a covalent bond to form a 4, 5, 6, 7, or 8-membered ring.

In certain embodiments, the present invention relates to the aforementioned method and any of the attendant definitions, wherein said prochiral aldehyde or prochiral ketone is represented by IV; and G is alkoxyl.

In certain embodiments, the present invention relates to the aforementioned method and any of the attendant definitions, wherein said prochiral aldehyde or prochiral ketone is represented by IV; and G is —OCH$_2$CH$_3$.

In certain embodiments, the present invention relates to the aforementioned method and any of the attendant definitions, wherein said prochiral aldehyde or prochiral ketone is represented by IV; and J is H, alkynyl or aryl.

In certain embodiments, the present invention relates to the aforementioned method and any of the attendant definitions, wherein said prochiral aldehyde or prochiral ketone is represented by IV; and J is H,

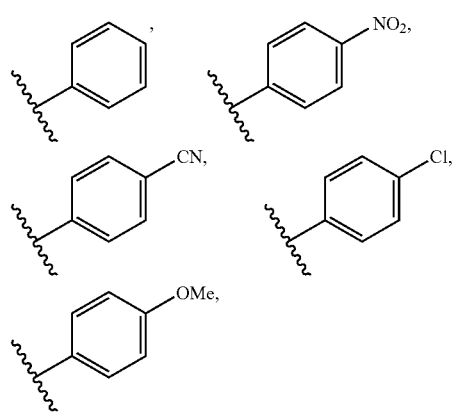

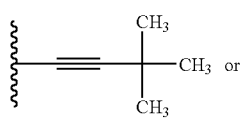

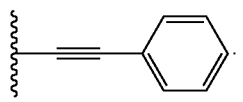

In certain embodiments, the present invention relates to the aforementioned method and any of the attendant definitions, wherein said prochiral aldehyde or prochiral ketone is represented by IV; G is alkoxyl; and J is H, alkynyl or aryl.

In certain embodiments, the present invention relates to the aforementioned method and any of the attendant definitions, wherein said prochiral aldehyde or prochiral ketone is represented by IV; G is —OCH$_2$CH$_3$; J is H,

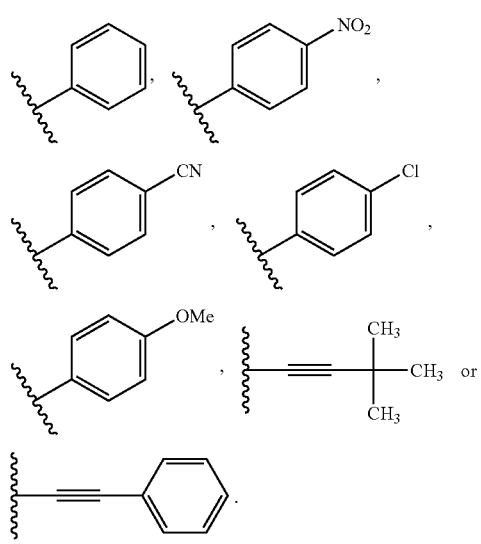

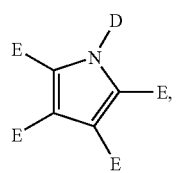, 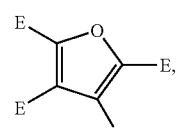

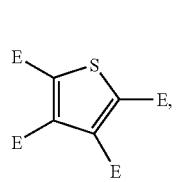

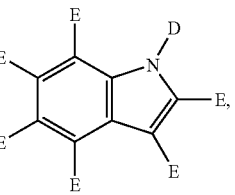.

In certain embodiments, the present invention relates to the aforementioned method and any of the attendant definitions, wherein said aromatic compound is selected from the group consisting of

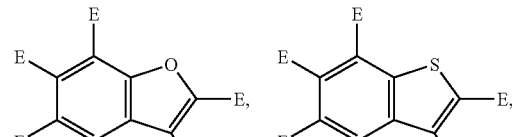

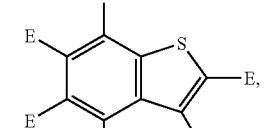

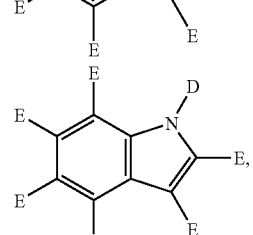

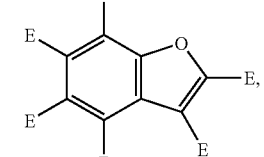

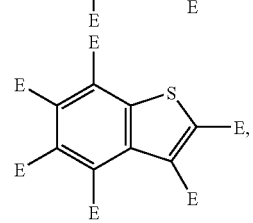

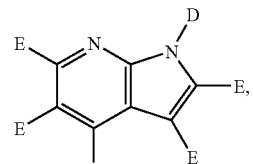

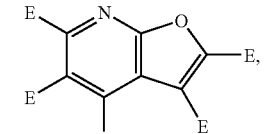

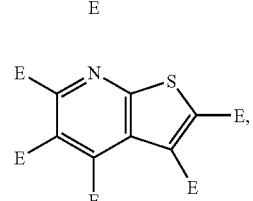 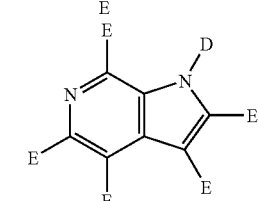

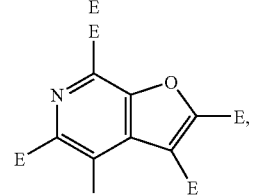 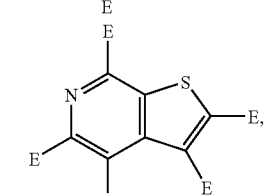

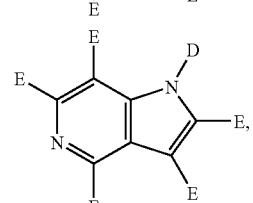 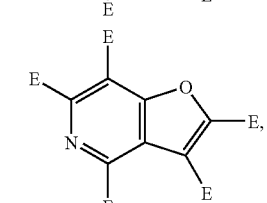

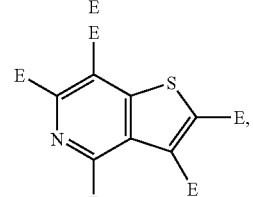 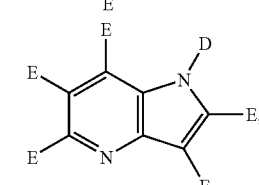

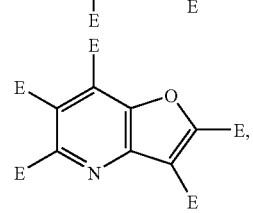 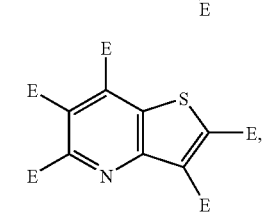

-continued

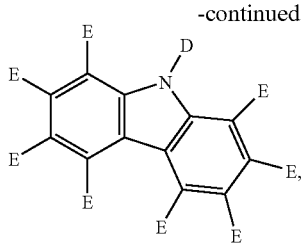

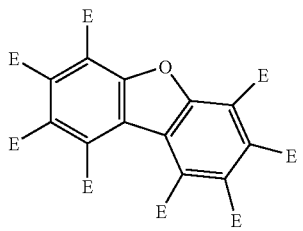

and

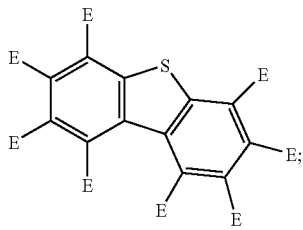

D is H, alkyl, aralkyl, carbonyl or acyl; and

E is, independently for each occurrence, H, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde or ester.

In certain embodiments, the present invention relates to the aforementioned method and any of the attendant definitions, wherein said aromatic compound is

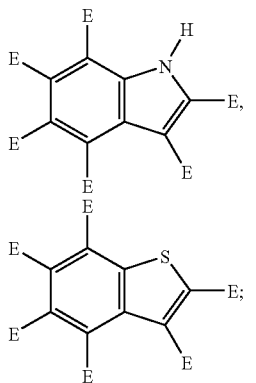

and E is, independently for each occurrence, H, alkyl, halogen or alkoxyl.

In certain embodiments, the present invention relates to the aforementioned method and any of the attendant definitions,

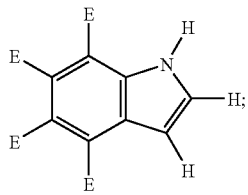

and E is, independently for each occurrence, H, alkyl, halogen or alkoxyl.

In certain embodiments, the present invention relates to the aforementioned method and any of the attendant definitions, wherein said aromatic compound is selected from the group consisting of

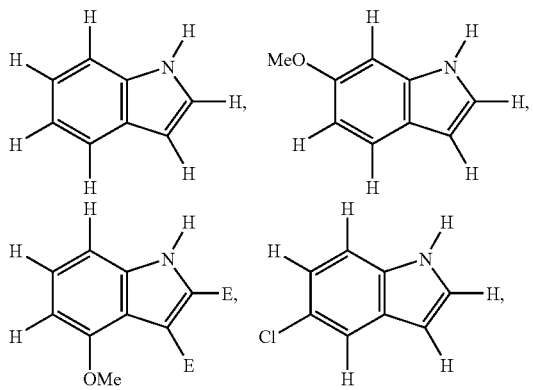

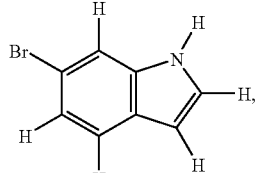

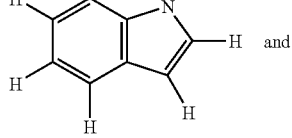

and

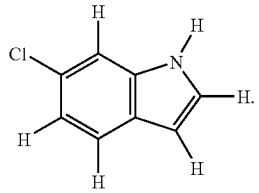

In certain embodiments, the present invention relates to the aforementioned method and any of the attendant definitions, wherein said aromatic compound is

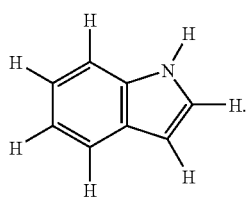

In certain embodiments, the present invention relates to the aforementioned method and any of the attendant definitions, wherein said catalyst is present in less than about 70 mol % relative to said prochiral aldehyde or prochiral ketone.

In certain embodiments, the present invention relates to the aforementioned method and any of the attendant definitions, wherein said catalyst is present in less than about 40 mol % relative to said prochiral aldehyde or prochiral ketone.

In certain embodiments, the present invention relates to the aforementioned method and any of the attendant definitions, wherein said catalyst is present in less than about 10 mol % relative to said prochiral aldehyde or prochiral ketone.

In certain embodiments, the present invention relates to the aforementioned method and any of the attendant definitions, wherein said catalyst is present in less than about 5 mol % relative to said prochiral aldehyde or prochiral ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said chiral, non-racemic alcohol has an enantiomeric excess or diastereomeric excess greater than about 95%.

One aspect of the present invention relates to a method of preparing a chiral, non-racemic alcohol from a prochiral aldehyde or prochiral ketone, comprising the step of:

reacting a prochiral aldehyde or prochiral ketone with an indole in the presence of a catalyst; thereby producing a chiral, non-racemic alcohol; wherein said catalyst is represented by formula II:

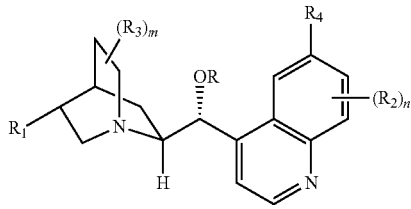

wherein, independently for each occurrence:

R represents hydrogen, alkyl, aryl, heteroaryl, aralkyl, heteroaralkyl, alkyloyl, aryloyl, arylalkyloyl, heteroaryloyl, or heteroarylalkyloyl;

$R_1$ represents alkyl, or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive;

$R_4$ represents —OH, —SH, or —NHR$_5$; and $R_5$ represents hydrogen, acyl or aralkyl.

In certain embodiments, the present invention relates to the aforementioned method and any of the attendant definitions, wherein $R_4$ represents OH.

In certain embodiments, the present invention relates to the aforementioned method and any of the attendant definitions, wherein $R_4$ represents OH; and R represents hydrogen, aryl, aralkyl, or aryloyl.

In certain embodiments, the present invention relates to the aforementioned method and any of the attendant definitions, wherein $R_4$ represents OH; and R represents —H,

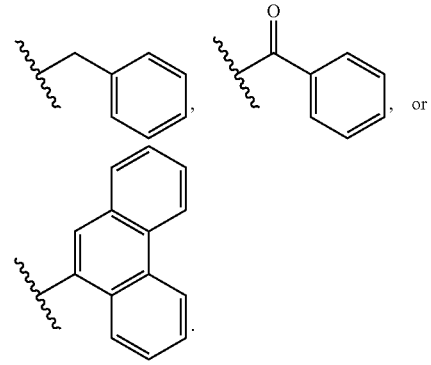

In certain embodiments, the present invention relates to the aforementioned method and any of the attendant definitions, wherein $R_4$ represents OH; and R represents

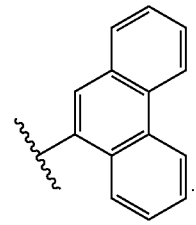 [SMILES: *c1cc2ccccc2c2ccccc12]

In certain embodiments, the present invention relates to the aforementioned method and any of the attendant definitions, wherein $R_4$ represents OH; and $R_1$ is alkyl.

In certain embodiments, the present invention relates to the aforementioned method and any of the attendant definitions, wherein $R_4$ represents OH; and $R_1$ is ethyl.

In certain embodiments, the present invention relates to the aforementioned method and any of the attendant definitions, wherein $R_4$ represents OH; and $R_1$ is alkenyl.

In certain embodiments, the present invention relates to the aforementioned method and any of the attendant definitions, wherein $R_4$ represents OH; and $R_1$ is —CH=CH$_2$.

In certain embodiments, the present invention relates to the aforementioned method and any of the attendant definitions, wherein $R_4$ represents OH; and n is 0.

In certain embodiments, the present invention relates to the aforementioned method and any of the attendant definitions, wherein $R_4$ represents OH; and m is 0.

In certain embodiments, the present invention relates to the aforementioned method and any of the attendant definitions, wherein $R_4$ represents OH; R is aryl and $R_1$ is ethyl.

In certain embodiments, the present invention relates to the aforementioned method and any of the attendant definitions, wherein $R_4$ represents OH; R is

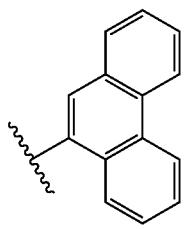

and R₁ is ethyl.

In certain embodiments, the present invention relates to the aforementioned method and any of the attendant definitions, wherein R₄ represents OH; R is aryl; and R₁ is —CH=CH₂.

In certain embodiments, the present invention relates to the aforementioned method and any of the attendant definitions, wherein R₄ represents OH; R is

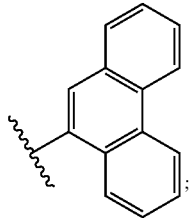 [SMILES: *c1cc2ccccc2c2ccccc12]

and R₁ is —CH=CH₂.

In certain embodiments, the present invention relates to the aforementioned method and any of the attendant definitions, wherein R₄ represents OH; R is aryl; R₁ is ethyl; m is 0; and n is 0.

In certain embodiments, the present invention relates to the aforementioned method and any of the attendant definitions, wherein R₄ represents OH; R is

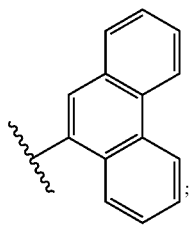 [SMILES: *c1cc2ccccc2c2ccccc12]

R₁ is ethyl; m is 0; and n is 0.

In certain embodiments, the present invention relates to the aforementioned method and any of the attendant definitions, wherein R₄ represents OH; R is aryl; R₁ is —CH=CH₂; m is 0; and n is 0.

In certain embodiments, the present invention relates to the aforementioned method and any of the attendant definitions, wherein R₄ represents OH; R is

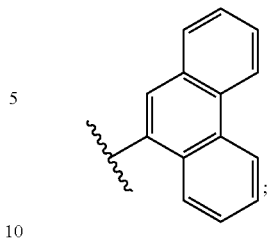

R₁ is —CH=CH₂; m is 0; and n is 0.

In certain embodiments, the present invention relates to the aforementioned method and any of the attendant definitions, wherein said prochiral aldehyde or prochiral ketone is represented by III:

wherein

X represents alkyl, aryl, heteroaryl, aralkyl, or heteroaralkyl; and

Z represents H, perfluoroalkyl, alkyl, aryl, heteroaryl, aralkyl, or heteroaralkyl.

In certain embodiments, the present invention relates to the aforementioned method and any of the attendant definitions, wherein said prochiral aldehyde or prochiral ketone is represented by III; and Z is H.

In certain embodiments, the present invention relates to the aforementioned method and any of the attendant definitions, wherein said prochiral aldehyde or prochiral ketone is represented by III; and X is aryl.

In certain embodiments, the present invention relates to the aforementioned method and any of the attendant definitions, wherein said prochiral aldehyde or prochiral ketone is represented by III; and X is a substituted or unsubstituted 6-membered single-ring aromatic group that may include from zero to four heteroatoms.

In certain embodiments, the present invention relates to the aforementioned method and any of the attendant definitions, wherein said prochiral aldehyde or prochiral ketone is represented by III; and X is a substituted or unsubstituted phenyl.

In certain embodiments, the present invention relates to the aforementioned method and any of the attendant definitions, wherein said prochiral aldehyde or prochiral ketone is represented by III; and X is

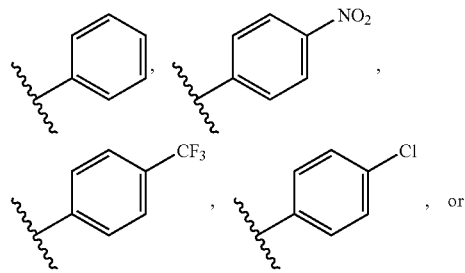

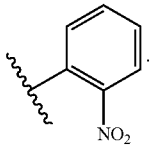

In certain embodiments, the present invention relates to the aforementioned method and any of the attendant definitions, wherein said prochiral aldehyde or prochiral ketone is represented by III; Z is H; and X is aryl.

In certain embodiments, the present invention relates to the aforementioned method and any of the attendant definitions, wherein said prochiral aldehyde or prochiral ketone is represented by III; Z is H; and X is

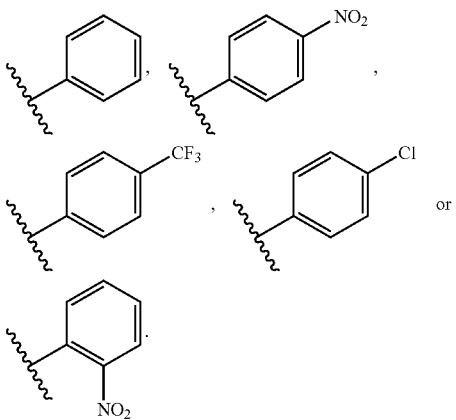

In certain embodiments, the present invention relates to the aforementioned method and any of the attendant definitions, wherein said prochiral aldehyde or prochiral ketone is represented by IV:

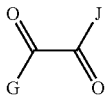

IV wherein

G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;

J represents H, perfluoroalkyl, alkyl, aryl, heteroaryl, aralkyl, or heteroaralkyl; and G and J may be connected by a covalent bond to form a 4, 5, 6, 7, or 8-membered ring.

In certain embodiments, the present invention relates to the aforementioned method and any of the attendant definitions, wherein said prochiral aldehyde or prochiral ketone is represented by IV; and G is alkoxyl.

In certain embodiments, the present invention relates to the aforementioned method and any of the attendant definitions, wherein said prochiral aldehyde or prochiral ketone is represented by IV; and G is —OCH$_2$CH$_3$.

In certain embodiments, the present invention relates to the aforementioned method and any of the attendant definitions, wherein said prochiral aldehyde or prochiral ketone is represented by IV; and J is H, alkynyl or aryl.

In certain embodiments, the present invention relates to the aforementioned method and any of the attendant definitions, wherein said prochiral aldehyde or prochiral ketone is represented by IV; and J is H,

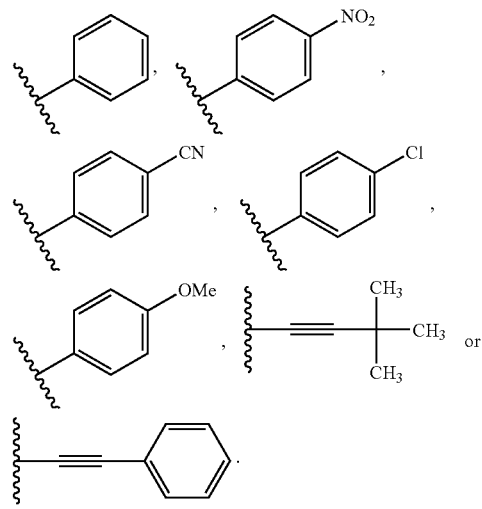

In certain embodiments, the present invention relates to the aforementioned method and any of the attendant definitions, wherein said prochiral aldehyde or prochiral ketone is represented by IV; G is alkoxyl; and J is H, alkynyl or aryl.

In certain embodiments, the present invention relates to the aforementioned method and any of the attendant definitions, wherein said prochiral aldehyde or prochiral ketone is represented by IV; G is —OCH$_2$CH$_3$; J is H,

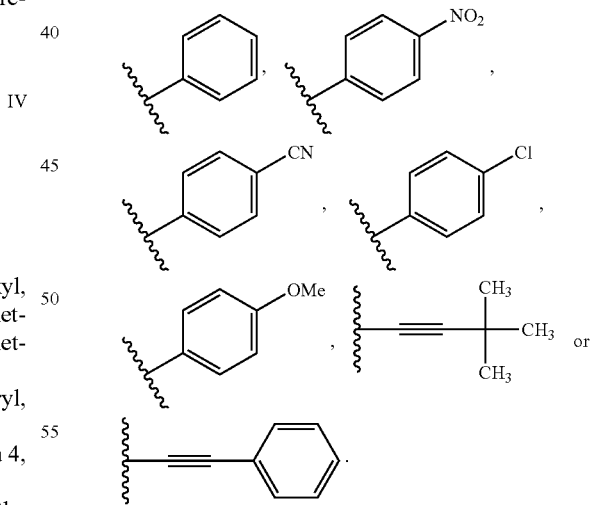

In certain embodiments, the present invention relates to the aforementioned method and any of the attendant definitions, wherein said catalyst is present in less than about 70 mol % relative to said prochiral aldehyde or prochiral ketone.

In certain embodiments, the present invention relates to the aforementioned method and any of the attendant definitions, wherein said catalyst is present in less than about 40 mol % relative to said prochiral aldehyde or prochiral ketone.

In certain embodiments, the present invention relates to the aforementioned method and any of the attendant definitions, wherein said catalyst is present in less than about 10 mol % relative to said prochiral aldehyde or prochiral ketone.

In certain embodiments, the present invention relates to the aforementioned method and any of the attendant definitions, wherein said catalyst is present in less than about 5 mol % relative to said prochiral aldehyde or prochiral ketone.

In certain embodiments, the present invention relates to the aforementioned method and any of the attendant definitions, wherein said chiral, non-racemic alcohol has an enantiomeric excess or diastereomeric excess greater than about 50%.

In certain embodiments, the present invention relates to the aforementioned method and any of the attendant definitions, wherein said chiral, non-racemic alcohol has an enantiomeric excess or diastereomeric excess greater than about 70%.

In certain embodiments, the present invention relates to the aforementioned method and any of the attendant definitions, wherein said chiral, non-racemic alcohol has an enantiomeric excess or diastereomeric excess greater than about 90%.

In certain embodiments, the present invention relates to the aforementioned method and any of the attendant definitions, wherein said-chiral, non-racemic alcohol has an enantiomeric excess or diastereomeric excess greater than about 95%.

Another aspect of the present invention relates to any one of the aforementioned methods of preparing a chiral, non-racemic alcohol from a prochiral aldehyde or prochiral ketone, wherein said catalyst is not represented by formula I or formula II, but instead is represented by formula VII or formula VIII:

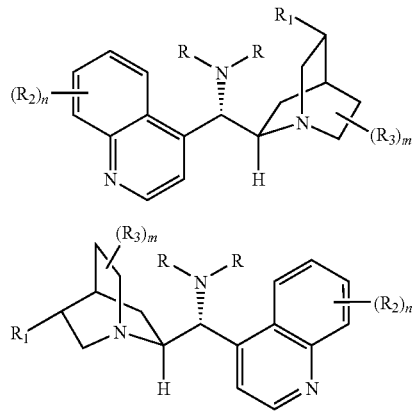

wherein, independently for each occurrence:

R represents H or a substituted or unsubstituted alkyl, alkenyl, alkynyl, aryl, aralkyl, heteroaryl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 6 inclusive; and m is an integer from 0 to 8 inclusive.

Another aspect of the present invention relates to any one of the aforementioned methods of preparing a chiral, non-racemic alcohol from a prochiral aldehyde or prochiral ketone, wherein said catalyst is not represented by formula I or formula II, but instead is represented by formula IX or formula X:

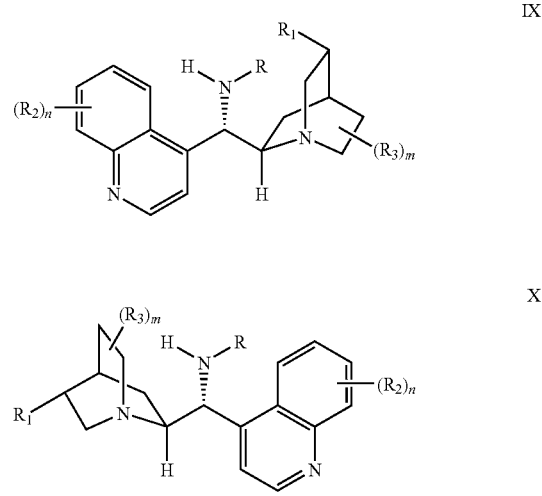

wherein, independently for each occurrence:

R represents —C(=S)N(H)-aryl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 6 inclusive; and m is an integer from 0 to 8 inclusive.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is selected from the group consisting of —C(=S)N(H)-(4-t-Bu-Ph), —C(=S)N(H)-(2-i-Pr-Ph), —C(=S)N(H)-(2-i-Pr-Ph), —C(=S)N(H)—(Ph), and —C(=S)N(H)-(3,5-bisCF$_3$-Ph).

In certain embodiments, the present invention relates to the aforementioned method and any of the attendant definitions, wherein said catalysts are not represented by formula I or II, but instead are selected from group consisting of the following catalysts:

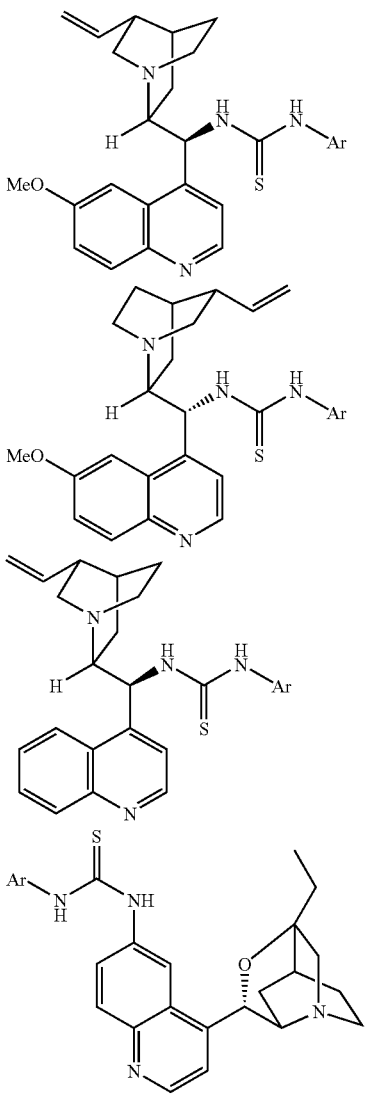

wherein Ar is selected from the group consisting of 4-tBuPh-, 2-iPrPh-, Ph-, and 3,5-bisCF₃Ph.

Substrates

A wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least one reactive electrophilic center or moiety with distinct stereogenic faces. The catalyzed, stereoselective attack of the nucleophile at the electrophilic center will produce a chiral non-racemic product. Most of the substrates contemplated for use in the methods of the present invention contain at least one carbonyl moiety. Examples of suitable carbonyl-containing substrates which are susceptible to nucleophilic attack by the subject method include ketones, aldehydes, aldehyde-ketones, diketones, keto-esters, aldehyde-esters, and the like.

In other embodiments, the electrophilic substrate will be a chiral compound. In certain embodiments, the substrate will be a racemic mixture. In certain embodiments, the substrate will be a mixture of diastereomers. In certain embodiments, the methods of the present invention effect a kinetic resolution. In certain embodiments, the methods of the present invention effect a dynamic kinetic resolution.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

General Information.

$^1$H and $^{13}$C NMR spectra were recorded on a Varian® instrument (400 MHz and 100 MHz, respectively) and internally referenced to tetramethylsilane signal or residual protio solvent signals. Data for $^1$H NMR are recorded as follows: chemical shift (δ, ppm), multiplicity (s, singlet; d, doublet; t, triplet; q, quartet; m, multiplet), intergration, coupling constant (Hz). Data for $^{13}$C NMR are reported in terms of chemical shift (δ, ppm). Infrared spectra were recorded on a Perkin Elmer FT-IR Spectrometer and are reported in frequency of absorption. Low resolution mass spectra for all the new compounds were performed by 70SE CI+, and were recorded and exact mass spectra on a 70-VSE-B high resolution mass spectrometer. Specific rotations were measured on a Jasco Digital Polarimeter.

High performance liquid chromatography (HPLC) analysis was performed on a Hewlett-Packard 1100 Series instrument equipped with a quaternary pump, using a Daicel Chiralcel OJ, OD Column (250×4.6 mm) or Chiralpak AD, AS Column (250×4.6 mm). UV absorption was monitored at 220 nm or at 254 nm.

Materials.

α-Ketoesters 3a, 3b were prepared according to literature procedures. Guo, M.; Li, D.; Zhang, Z. *J. Org. Chem.* 2003, 68, 10172-10174. α-Ketoesters 3c-g and aldehydes 5d-f were commercially available and purified by flash chromatography (silica gel 60, 0.040-0.063 mm, purchased from EM SCIENCE Inc.) before they were used for the Friedel-Crafts reaction. Aldehyde 5a was used as ~50% solution in toluene, which was commercially available. Indoles 2, aldehydes 5b-c and quinidine (QD), cinchonine (CN) were commercially available and used without any further purification. C6'-OH cinchona alkaloids Q-1a-d and QD-1a-d were prepared following procedures reported from these laboratories. H. Li, Y. Wang, L. Tang, L. Deng, *J. Am. Chem. Soc.* 2004, 126, 9906-9907; H. Li, Y. Wang, L. Tang, F. Wu, X. Liu, C. Guo, B. M. Foxman, L. Deng, *Angew. Chem.* 2005, 117, 107-110; *Angew.* *Chem. Int. Ed.* 2005, 44, 105-108; X. Liu, H. Li, L. Deng, *Org. Lett.* 2005, 7, 167-169; H. Li, J. Song, X. Liu, L. Deng, *J. Am. Chem. Soc.* 2005, 127, 8948-8949; H. Li, B. Wang, L. Deng, *J. Am. Chem. Soc.* 2006, 128, 732; and F. Wu, H. Li, R. Hong, L. Deng, *Angew. Chem.* 2006, 118, 961; *Angew. Chem. Int. Ed.* 2006, 45, 947.

Example 1

General Procedure for Friedel-Crafts Addition of Indoles to α-Ketoesters

At room temperature to the solution of pyruvates 3a-d (0.2 mmol) in Et$_2$O (0.4 mL) was added Q-1d or QD-1d (10 mol %) and followed by addition of indoles (0.4 mmol). Then the mixture was let stand at room temperature for 40-72 hours (as indicated in Table 1, entries 1-10). The reaction mixture was subjected to flash chromatography to afford the desired product 4. For entries 12 and 14 in Table 1, 0.02 mL of Et$_2$O was added to the reaction mixture. For entries 13, 15, 17, 18, these reactions were carried out at 70° C. in 0.02 mL of t-butyl methyl ether (TBME). For entries 16, the reaction was carried out at 70° C. in 0.05 mL of t-butyl methyl ether (TBME). See FIG. 3.

Example 2

General Procedure for Friedel-Crafts Addition of Indoles to Aldehydes

At room temperature to a solution of the aldehyde (5a-d) (0.2 mmol) in TBME (0.02 mL) was added Q-1d or QD-1d (10 mol %) and followed by the addition of the indoles (0.4 mmol). Then the mixture was allowed to stand at room temperature for 4-72 hours (as indicated in Table 2, entries 1-6) or at 70° C. for 40-48 h (entries 7-8, Table 2). The reaction mixture was subjected to flash chromatography to afford the desired product 6. See FIG. 4.

Example 3

Data for Products 4 and 6

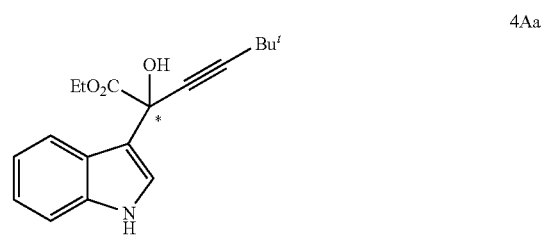

4Aa (−)-4Aa was obtained in 89% yield as a foam after flash chromatography (elution solvent: Ethyl Acetate/Hexanes=1/3) and 87% ee as determined by HPLC analysis [Chiralpak AD, Hexanes:IPA, 75:25, 1.0 mL/min, λ 220 nm, t (minor)=14.2 min, t (major)=7.7 min] from a reaction catalyzed by Q-1d (10 mol %) at room temperature for 63 hours. $[\alpha]_D^{25}=-1.8$ (c 1.0, CHCl$_3$); $^1$H NMR (400 MHz, CDCl$_3$) δ 8.14 (br, 1H), 7.76 (d, J=8.0 Hz, 1H), 7.44-7.42 (m, 1H), 7.34-7.32 (m, 1H), 7.19 (t, J=7.2 Hz, 1H), 7.11 (t, J=7.2 Hz, 1H), 4.39-4.31 (m, 1H), 4.17-4.09 (m, 1H), 4.07 (s, 1H), 1.29 (s, 9H), 1.21 (t, J=7.2 Hz, 3H); $^{13}$C NMR (100 MHz, CDCl$_3$) δ 172.5, 136.8, 124.4, 123.9, 122.2, 120.2, 119.8, 115.7, 111.3, 93.8, 77.2, 68.9, 63.0, 30.7, 27.5, 13.8; IR (CHCl$_3$) ν 3408 (br), 3058, 2970, 2242, 1731, 1619, 1543, 1458, 1255, 1033; HRMS (CI) m/z calcd. for (C$_{18}$H$_{21}$NO$_3$+H$^+$): 300.1599. found: 300.1592. (+)-4Aa was obtained as a foam in 96% yield and 88% ee from a reaction catalyzed by QD-1d (10 mol %) at room temperature for 62 hours.

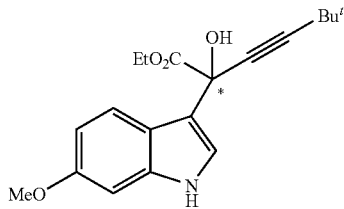

4Ba (+)-4Ba was obtained in 79% yield as a foam after flash chromatography (elution solvent: Ethyl Acetate/Hexanes=1/4) and 88% ee as determined by HPLC analysis [Chiralcel OD, Hexanes:IPA, 90:10, 1.0 mL/min, λ 220 nm, t (minor) 14.6 min, t (major) 16.5 min] from a reaction catalyzed by QD-1d (10 mol %) at room temperature for 40 hours. [α]$_D^{25}$=+3.6 (c 1.08, CHCl$_3$); $^1$H NMR (400 MHz, CDCl$_3$) δ 8.07 (s, 1H), 7.62 (d, J=8.8 Hz, 1H), 7.22 (d, J=2.4 Hz, 1H), 6.76 (dd, J=8.8 Hz, 2.4 Hz, 1H), 6.68 (d, J=2.4 Hz, 1H), 4.35-4.29 (m, 1H), 4.14-4.08 (m, 1H), 4.09 (s, 1H), 3.76 (s, 3H), 1.25 (s, 9H), 1.21-1.16 (m, 3H); $^{13}$C NMR (100 MHz, CDCl$_3$) δ172.5, 156.3, 137.6, 122.7, 120.7, 118.7, 115.7, 109.9, 94.5, 93.7, 77.2, 68.9, 63.0, 55.4, 30.6, 27.5, 13.8; IR (CHCl$_3$) ν 3405 (br), 2970, 2869, 2246, 1731, 1630, 1547, 1456, 1254, 1032. (−)-4Ba was obtained as a foam in 86% yield and 84% ee from a reaction catalyzed by Q-1d (10 mol %) at room temperature for 40 hours.

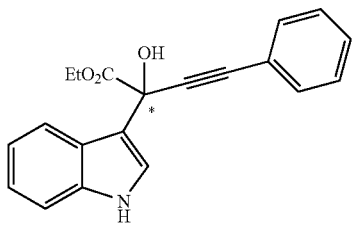

4Ab (+)-4Ab This product was obtained in 79% yield as a foam after flash chromatography (elution solvent: Ethyl Acetate/Hexanes=1/3) and 88% ee as determined by HPLC analysis [Chiralpak AD, Hexanes:IPA, 70:30, 1.0 mL/min, λ 220 nm, t (minor)=17.9 min, t (major)=14.2 min] from a reaction catalyzed by Q-1d (10 mol %) at room temperature for 44 hours. [α]$_D^{25}$=+14.2 (c 1.0, CHCl$_3$); $^1$H NMR (400 MHz, CDCl$_3$) δ 8.20 (br, 1H), 7.83 (d, J=8.0 Hz, 1H), 7.53-7.50 (m, 3H), 7.37-7.31 (m, 4H), 7.21 (t, J=7.2 Hz, 1H), 7.14 (t, J=7.2 Hz, 1H), 4.40-4.32 (m, 1H), 4.26 (s, 1H), 4.27-4.19 (m, 1H), 1.23 (t, J=7.2 Hz, 3H); $^{13}$C NMR (100 MHz, CDCl$_3$) δ 172.0, 136.8, 131.9, 128.8, 128.3, 124.4, 124.1, 122.3, 122.0, 120.1, 115.2, 111.4, 87.3, 84.8, 69.4, 63.4, 13.9; IR (CHCl$_3$) ν 3403 (br), 3060, 2981, 2226, 1729, 1596, 1458, 1242. (−)-4Ab was obtained as a foam in 80% yield and 90% ee from a reaction catalyzed by QD-1d (10 mol %) at room temperature for 43 hours.

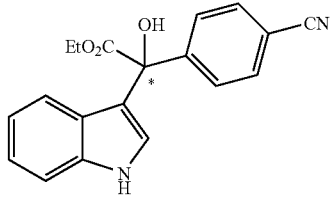

4Ac (+)-4Ac was obtained as a white powder in 88% yield after flash chromatography (elution solvent: Ethyl Acetate/Hexanes=1/2) and 97% ee as determined by HPLC analysis [Chiralcel OD, Hexanes:IPA, 80:20, 1.0 mL/min, λ 220 nm, t (minor)=12.5 min, t (major)=15.6 min] from a reaction catalyzed by Q-1d (10 mol %) at room temperature for 56 hours. [α]$_D^{25}$=+30.0 (c 1.0, CHCl$_3$); $^1$H NMR (400 MHz, CDCl$_3$) δ 8.17 (br, 1H), 7.74 (d, J=8.8 Hz, 2H), 7.63 (d, J=8.8 Hz, 2H), 7.38 (d, J=7.6 Hz, 1H), 7.35 (d, J=7.6 Hz, 1H), 7.20 (t, J=7.6 Hz, 1H), 7.12 (d, J=2.4 Hz, 1H), 7.04 (t, J=7.6 Hz, 1H), 4.33 (q, J=7.2 Hz, 2H), 4.28 (s, 1H), 1.26 (t, J=7.2 Hz, 3H); $^{13}$C NMR (100 MHz, CDCl$_3$) δ 173.5, 146.4, 136.7, 131.8, 127.9, 125.0, 123.6, 122.6, 120.5, 120.1, 118.7, 116.8, 111.7, 111.4, 77.3, 63.2, 14.0; IR (CHCl$_3$) ν 3406 (br), 2983, 2230 (CN), 1727, 1605, 1458, 1241; HRMS (CI) m/z calcd. for (C$_{19}$H$_{16}$N$_2$O$_3$+H$^+$): 321.1239. found: 321.1243. (−)-4Ac was obtained as a white powder in 77% yield and 97% ee from a reaction catalyzed by QD-1d (10 mol %) at room temperature for 55 hours.

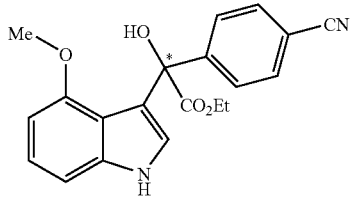

4Cc (−)-4 Cc was obtained in 79% yield as a white powder after flash chromatography (elution solvent: Ethyl Acetate/Hexanes=1/2) and 99% ee as determined by HPLC analysis [Chiralpak AD, Hexanes:IPA, 75:25, 1.0 mL/min, λ 220 nm, t (minor)=11.5 min, t (major)=13.2 min] from a reaction catalyzed by Q-1d (10 mol %) at room temperature for 64 hours. [α]$_D^{25}$=−95.8 (c 1.0, CHCl$_3$); $^1$H NMR (400 MHz, CDCl$_3$) δ 8.06 (br, 1H), 7.86 (d, J=8.8 Hz, 2H), 7.67 (d, J=8.8 Hz, 2H), 7.16 (t, J=8.0 Hz, 1H), 7.02 (d, J=8.0 Hz, 1H), 6.55 (d, J=8.0 Hz, 1H), 6.54 (d, J=2.4 Hz, 1H), 5.05 (s, 1H), 4.31-4.24 (m, 2H), 3.86 (s, 3H), 1.25 (t, J=7.2 Hz, 3H); $^{13}$C NMR (100 MHz, CDCl$_3$) δ 172.9, 152.0, 146.4, 138.4, 131.7, 127.4, 123.7, 123.0, 118.9, 118.8, 115.4, 111.6, 105.4, 100.5, 62.2, 55.1, 14.1; IR (CHCl$_3$) ν 3397 (br), 2981, 2228, 1732, 1619, 1587, 1508, 1236, 1091; HRMS (CI) m/z calcd. for (C$_{20}$H$_{18}$N$_2$O$_4$+H$^+$): 351.1345. found: 351.1349. (+)-4 Cc was obtained as a white powder in 79% yield and 99% ee from a reaction catalyzed by QD-1d (10 mol %) at room temperature for 64 hours.

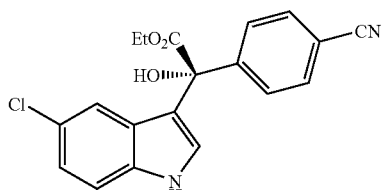

(−)-(R)-4Dc (−)-(R)-4Dc was obtained in 85% yield as a white powder after flash chromatography (elution solvent: Ethyl Acetate/Hexane=1/2) and 96% ee as determined by HPLC analysis [Chiralpak AD, Hexanes:IPA, 80:20, 1.0 mL/min, λ 220 nm, t (minor) 15.3 min, t (major)=13.0 min] from a reaction catalyzed by Q-1d (10 mol %) at room temperature for 71 hours. $[\alpha]_D^{25}$=−1.4 (c 1.1, CHCl$_3$); $^1$H NMR (400 MHz, CDCl$_3$) δ 8.19 (br, 1H), 7.70 (d, J=8.0 Hz, 2H), 7.64 (d, J=8.0 Hz, 2H), 7.38 (s, 1H), 7.30 (d, J=9.2 Hz, 1H), 7.17-7.15 (m, 2H), 4.33 (q, J=7.2 Hz, 2H), 4.31 (s, 1H), 1.27 (t, J=7.2 Hz, 3H); $^{13}$C NMR (100 MHz, CDCl$_3$) δ 173.3, 146.1, 135.1, 131.9, 127.8, 126.2, 126.0, 124.8, 123.2, 120.2, 118.6, 116.7, 112.4, 112.0, 77.1, 63.5, 14.0; IR (CHCl$_3$) ν 3413 (br), 2983, 2231, 1729, 1606, 1569, 1464, 1239; HRMS (CI) m/z calcd. for (C$_{19}$H$_{15}$N$_2$O$_3$Cl+H$^+$): 355.0849. found: 355.0855.

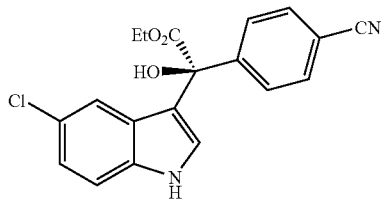

(+)-(S)-4Dc (+)-(S)-4Dc was obtained as a white powder in 96% yield and 94% ee from a reaction catalyzed by QD-1d (10.0 mol %) at room temperature for 70 hours. The absolute configuration of (+)-4Dc was determined to be S by X-ray analysis (see below).

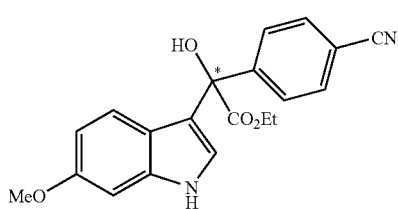

4Bc (+)-4Bc was obtained in 97% yield as a thick oil after flash chromatography (elution solvent: Ethyl Acetate/Hexanes=1/2) and 97% ee as determined by HPLC analysis [Chiralpak AD, Hexanes:IPA, 65:35, 1.0 mL/min, λ 220 nm, t (minor)=13.4 min, t (major)=16.0 min] from a reaction catalyzed by Q-1d (10 mol %) at room temperature for 58 hours. $[\alpha]_D^{25}$=+25.1 (c 1.3, CHCl$_3$); $^1$H NMR (400 MHz, CDCl$_3$) δ 8.03 (br, 1H), 7.73 (d, J=8.4 Hz, 2H), 7.62 (d, J=8.4 Hz, 2H), 7.21 (d, J=8.4 Hz, 1H), 7.00 (d, J=2.0 Hz, 1H), 6.85 (d, J=2.0 Hz, 1H), 6.70 (dd, J=2.0 Hz, 8.4 Hz, 1H), 4.32 (q, J=−7.2 Hz, 2H), 4.25 (s, 1H), 3.82 (s, 3H), 1.26 (t, J=7.2 Hz, 3H); $^{13}$C NMR (100 MHz, CDCl$_3$) δ 173.5, 156.6, 146.5, 137.5, 131.7, 127.9, 122.4, 121.2, 119.4, 118.7, 116.8, 111.6, 110.1, 94.6, 77.3, 63.2, 55.5, 14.0; IR (CHCl$_3$) ν 3405 (br), 2982, 2229, 1727, 1629, 1544, 1457, 1257; HRMS (CI) m/z calcd. for (C$_{20}$H$_{18}$N$_2$O$_4$+H$^+$): 351.1345. found: 351.1352. (−)-4Bc was obtained as a thick oil in 97% yield and 96% ee from a reaction catalyzed by QD-1d (10 mol %) at room temperature for 59 hours.

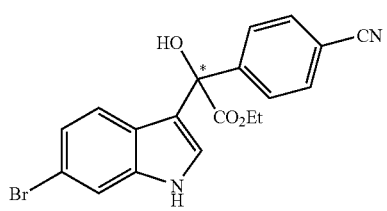

4Ec (+)-4Ec was obtained in 67% yield as a white powder after flash chromatography (elution solvent: Ethyl Acetate/Hexanes=1/2) and 95% ee as determined by HPLC analysis [Chiralpak AD, Hexanes:IPA, 70:30, 0.9 mL/min, λ 254 nm, t (minor)=11.4 min, t (major)=13.4 min] from a reaction catalyzed by Q-1d (10 mol %) at room temperature for 61 hours. $[\alpha]_D^{25}$+13.8 (c 1.0, CHCl$_3$); $^1$H NMR (400 MHz, CDCl$_3$) δ 8.18 (br, 1H), 7.70 (d, J=8.4 Hz, 2H), 7.63 (d, J=8.4 Hz, 2H), 7.54 (s, 1H), 7.22 (d, J=8.4 Hz, 1H), 7.13 (d, J=8.4 Hz, 1H), 7.11 (br, 1H), 4.32 (q, J=7.2 Hz, 2H), 4.31 (s, 1H), 1.26 (t, J=7.2 Hz, 3H); $^{13}$C NMR (100 MHz, CDCl$_3$) δ 173.3, 146.2, 137.5, 131.9, 127.8, 124.1, 124.0, 123.5, 121.9, 118.6, 117.1, 116.3, 114.3, 111.9, 77.1, 63.4, 14.0; IR (CHCl$_3$) ν 3411 (br), 2982, 2230, 1728, 1607, 1539, 1454, 1252; HRMS (CI) m/z calcd. for (C$_{19}$H$_{15}$N$_2$O$_3$Br+H$^+$): 399.0344. found: 399.0335. (−)-4Ec This product was obtained as a white powder in 80% yield and 95% ee from a reaction catalyzed by QD-1d (10 mol %) at room temperature for 61 hours.

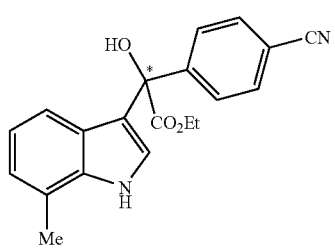

4Fc (+)-4Fc was obtained in 96% yield as a thick oil after flash chromatography (elution gradient: Ethyl Acetate/Hexanes=1/2) and 97% ee as determined by HPLC analysis [Chiralpak AD, Hexanes:IPA, 75:25, 1.0 mL/min, λ 220 nm, t (minor)=14.7 min, t (major)=16.8 min] from a reaction catalyzed by Q-1d (10 mol %) at room temperature for 66 hours. $[\alpha]_D^{25}$=+32.9 (c 1.3, CHCl$_3$); $^1$H NMR (400 MHz, CDCl$_3$) δ 8.11 (br, 1H), 7.74 (d, J=6.8 Hz, 2H), 7.62 (d, J=6.8 Hz, 2H), 7.19 (d, J=8.0 Hz, 1H), 7.12 (d, J=2.4 Hz, 1H), 7.01 (d, J=6.8 Hz, 1H), 6.96 (t, J=8.0 Hz, 1H), 4.32 (q, J=6.8 Hz, 2H), 4.26 (s, 1H), 2.49 (s, 3H), 1.26 (t, J=6.8 Hz, 3H); $^{13}$C NMR (100 MHz, CDCl$_3$) δ 173.6, 146.5, 136.3, 131.8, 128.0, 124.6, 123.3, 123.1, 120.5, 120.4, 118.8, 118.3, 117.4, 111.7, 63.2, 16.5, 14.0; IR (CHCl$_3$) ν 3405 (br), 2981, 2230, 1727, 1605, 1498, 1248; HRMS (CI) m/z calcd. for (C$_{20}$H$_{18}$N$_2$O$_3$+H$^+$): 335.1395. found: 335.1391. (−)-4Fc was obtained as a thick oil in 85% yield and 97% ee from a reaction catalyzed by QD-1d (10 mol %) at room temperature for 66 hours.

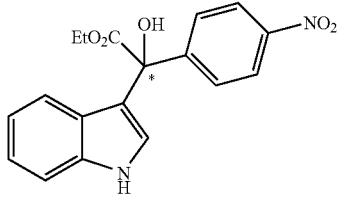

4Ad (+)-4Ad was obtained as a yellow powder in 88% yield after flash chromatography (elution solvent: Ethyl Acetate/Hexanes=1/3) and 98% ee as determined by HPLC analysis [Chiralcel AS, Hexanes:IPA, 80:20, 1.0 mL/min, λ 220 nm, t (minor)=16.7 min, t (major)=22.7 min] from a reaction catalyzed by Q-1d (10 mol %) at room temperature for 72 hours. $[\alpha]_D^{25}$=+30 (c 1.28, CHCl$_3$); $^1$H NMR (400 MHz, CDCl$_3$) δ 8.20 (br, 1H), 8.18 (d, J=9.2 Hz, 2H), 7.80 (d, J=9.2 Hz, 2H), 7.36 (t, J=8.4 Hz, 2H), 7.20 (t, J=7.6 Hz, 1H), 7.11-7.10 (m, 1H), 7.03 (t, J=7.2 Hz, 1H), 4.33 (q, J=7.2 Hz, 2H), 4.32 (s, 1H), 1.26 (t, J=7.2 Hz, 3H); $^{13}$C NMR (100 MHz, CDCl$_3$) δ 173.4, 148.3, 147.5, 136.7, 128.2, 125.0, 123.5, 123.1, 122.7, 120.5, 120.2, 116.9, 111.4, 77.2, 63.3, 13.4; IR (CHCl$_3$) ν 3410 (br), 2983, 1727, 1596, 1520, 1349, 1243; HRMS (CI) m/z calcd. for (C$_{18}$H$_{16}$N$_2$O$_5$+H$^+$): 341.1137. found: 321.1143. (−)-4Ad was obtained as a yellow powder in 95% yield and 95% ee from a reaction catalyzed by QD-1d (10 mol %) at room temperature for 71 hours.

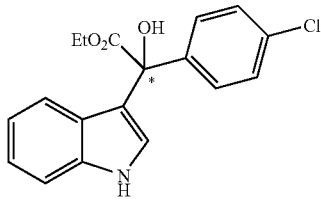

4Ae (−)-4Ae was obtained as a white powder in 93% yield after flash chromatography (elution solvent: Ethyl Acetate/Hexanes=1/3) and 95% ee as determined by HPLC analysis [Chiralpak OD+OD, Hexanes:IPA, 85:15, 0.9 mL/min, λ 220 nm, t (minor)=29.7 min, t (major)=26.7 min] from a reaction catalyzed by QD-1d (10 mol %) at room temperature for 88 hours. $[\alpha]_D^{25}$=−5.9 (c 1.2, CHCl$_3$); $^1$H NMR (400 MHz, CDCl$_3$) δ 8.15 (br, 1H), 7.56-7.54 (m, 2H), 7.41 (d, J=8.4 Hz, 1H), 7.33-7.30 (m, 3H), 7.18 (t, J=7.2 Hz, 1H), 7.04 (t, J=7.2 Hz, 1H), 7.00 (d, J=2.4 Hz, 1H), 4.32-4.29 (m, 3H), 1.24 (t, J=6.8 Hz, 3H); $^{13}$C NMR (100 MHz, CDCl$_3$) δ 175.0, 140.5, 137.4, 134.6, 129.2, 128.9, 126.0, 124.5, 123.1, 121.5, 120.7, 118.2, 111.9, 77.8, 63.7, 14.7; IR (CHCl$_3$) ν 3407 (br), 3059, 2982, 1722, 1543, 1489, 1458, 1242, 1092. (+)-4Ae was obtained as a white powder in 95% yield and 95% ee from a reaction catalyzed by Q-1d (10 mol %) at room temperature for 72 hours. (−)-4Ae was obtained as a white powder in 96% yield and 86% ee from a reaction catalyzed by QD-1d (10 mol %) at 70° C. for 24 hours. (+)-4Ae was obtained as a white powder in 97% yield and 89% ee from a reaction catalyzed by Q-1d (10 mol %) at 70° C. for 24 hours.

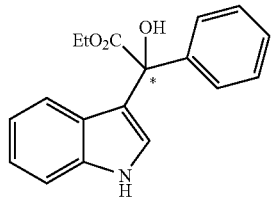

4Af (−)-4Af was obtained as a white powder in 63% yield after flash chromatography (elution solvent: Ethyl Acetate/Hexanes=1/3) and 94% ee as determined by HPLC analysis [Chiralpak AD, Hexanes:IPA, 80:20, 1.0 mL/min, λ 220 nm, t (minor)=9.8 min, t (major)=14.7 min] from a reaction catalyzed by Q-1d (10 mol %) at room temperature for 88 hours. $[\alpha]_D^{25}$=−11.5 (c 0.95, CHCl$_3$); $^1$H NMR (400 MHz, CDCl$_3$) δ 8.15 (br, 1H), 7.63-7.61 (m, 2H), 7.44 (d, J=8.4 Hz, 1H), 7.36-7.34 (m, 3H), 7.30 (d, J=7.6 Hz, 1H), 7.17 (t, J=7.6 Hz, 1H), 7.04 (t, J=7.6 Hz, 1H), 6.98 (d, J=2.4 Hz, 1H), 4.32-4.29 (m, 3H), 1.23 (t, J=7.2 Hz, 3H); $^{13}$C NMR (100 MHz, CDCl$_3$) δ 175.5, 141.9, 137.4, 128.7, 128.6, 127.6, 126.2, 124.8, 122.9, 121.6, 120.5, 118.4, 111.9, 78.2, 63.5, 14.7; IR (CHCl$_3$) ν 3408 (br), 3058, 2981, 1720, 1543, 1493, 1458, 1241, 1095. (+)-4Af was obtained as a white powder in 71% yield and 93% ee from a reaction catalyzed by QD-1d (10.0 mol %) at room temperature for 88 hours.

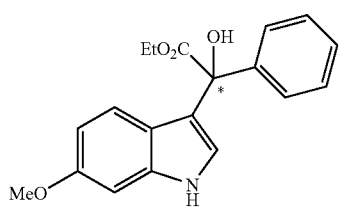

4Bf (−)-4Bf was obtained in 92% yield after flash chromatography (elution solvent: Ethyl Acetate/Hexane=1/2) and 84% ee as determined by HPLC analysis [Chiralpak AD, Hexanes:IPA, 70:30, 1.0 mL/min, λ 220 nm, t (minor)=18.7 min, t (major)=12.6 min] from a reaction catalyzed by Q-1d (10 mol %) at 70° C. for 28 hours. $[\alpha]_D^{25}$=−6.8 (c 0.5, CHCl$_3$); $^1$H NMR (400 MHz, CDCl$_3$) δ 8.05 (s, 1H), 7.59-7.56 (m, 2H), 7.34-7.26 (m, 4H), 6.85 (d, J=3.2 Hz, 1H), 6.72 (d, J=1.6 Hz, 1H), 6.67 (dd, J=8.4 Hz, 2.4 Hz, 1H), 4.29-4.24 (m, 2H), 4.26 (s, 1H), 3.77 (s, 3H), 1.21 (t, J=7.2 Hz, 3H); $^{13}$C NMR (100 MHz, CDCl$_3$) δ 174.8, 156.4, 141.3, 137.5, 128.0, 127.9, 126.9, 122.9, 121.5, 119.8, 117.6, 109.8, 94.4, 77.5, 62.8, 55.5, 14.0; IR (CHCl$_3$) ν 3405 (br), 2981, 2834, 1718, 1634, 1558, 1576, 1258; HRMS (EI) m/z calcd. for (C$_{19}$H$_{19}$NO$_4$): 325.1314. found: 325.1306. (+)-4Bf was obtained in 72% yield and 82% ee from a reaction catalyzed by QD-1d (10.0 mol %) at 70° C. for 29 hours.

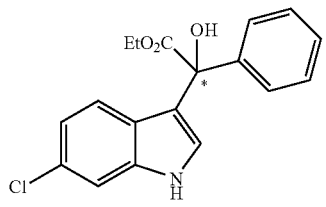

4Gf (−)-4 Gf was obtained in 96% yield after flash chromatography (elution solvent: Ethyl Acetate/Hexane=1/3) and 84% ee as determined by HPLC analysis [Chiralpak AD, Hexanes: IPA, 70:30, 1.0 mL/min, λ 220 nm, t (minor)=15.4 min, t (major)=9.5 min] from a reaction catalyzed by Q-1d (10 mol %) at 70° C. for 51 hours. $[\alpha]_D^{25}=-14$ (c 1.0, CHCl$_3$); $^1$H NMR (400 MHz, CDCl$_3$) δ 8.22 (br, 1H), 7.55-7.53 (m, 2H), 7.35-7.30 (m, 4H), 7.24 (d, J=1.6 Hz, 1H), 6.98-6.96 (m, 2H), 4.31 (s, 1H), 4.30-4.26 (m, 2H), 1.21 (t, J=7.2 Hz, 3H); $^{13}$C NMR (100 MHz, CDCl$_3$) δ 174.5, 141.0, 137.0, 128.2, 128.1, 126.8, 124.7, 124.1, 121.8, 120.6, 117.9, 111.1, 77.4, 62.9, 14.0; IR (CHCl$_3$) v 3419 (br.), 2981, 1718, 1449, 1255, 1095; HRMS (EI) m/z calcd. for (C$_{18}$H$_{16}$NO$_3$): 329.0819. found:): 329.0819. (+)-4 Gf was obtained in 87% yield and 81% ee from a reaction catalyzed by QD-1d (10.0 mol %) at 70° C. for 51 hours.

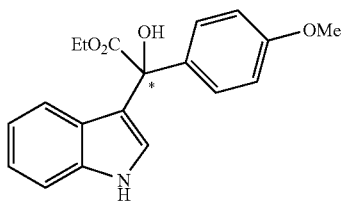

4Ag (−)-4Ag was obtained in 52% yield after flash chromatography (elution solvent: Ethyl Acetate/Hexane=1/3) and 83% ee as determined by HPLC analysis [Chiralpak AD, Hexanes: IPA, 60:40, 1.0 mL/min, λ 220 nm, t (minor)=14.5 min, t (major)=10.1 min] from a reaction catalyzed by Q-1d (10 mol %) at 70° C. for 56 hours. $[\alpha]_D^{25}=-8.4$ (c 0.7, CHCl$_3$); $^1$H NMR (400 MHz, CDCl$_3$) δ 8.11 (br, 1H), 7.49 (d, J=8.4 Hz, 2H), 7.44 (d, J=8.0 Hz, 1H), 7.34 (d, J=8.0 Hz, 1H), 7.17 (t, J=8.0 Hz, 1H), 7.10 (d, J=2.4 Hz, 1H), 7.04 (t, J=8.0 Hz, 1H), 6.86 (t, J=8.4 Hz, 2H), 4.30-4.28 (m, 2H), 4.21 (s, 1H), 3.81 (s, 3H), 1.25-1.21 (t, J=7.6 Hz, 3H); $^{13}$C NMR (100 MHz, CDCl$_3$) δ 175.7, 159.9, 137.4, 134.2, 128.9, 126.3, 124.6, 122.9, 121.8, 120.5, 118.8, 114.0, 111.8, 77.9, 63.4, 55.9, 14.7; IR (CHCl$_3$) v 3408 (br.) 2981, 1722, 1609, 1510, 1459, 1249, 1033.

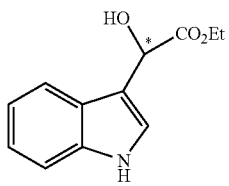

6Aa (−)-6Aa was obtained as a colorless oil in 95% yield after flash chromatography (elution solvent: ethyl acetate/hexanes=1/2) and 93% ee as determined by HPLC analysis [Daicel chiralcel OD, hexanes:IPA, 90:10, 1.0 mL/min, λ 220 nm, t (major)=35.8 min, t (minor)=45.2 min] from a reaction catalyzed by Q-1d (10 mol %) at room temperature for 6 hours. $[\alpha]_D^{25}=-95.5$ (c 0.8, CHC$_3$); 1H NMR (400 MHz, CDCl$_3$) δ 8.22 (br, 1H), 7.71 (d, J=8.0 Hz, 1H), 7.34 (t, J=8.0 Hz, 1H), 7.26-7.06 (m, 3H), 5.47 (d, J=6.0 Hz, 1H), 4.43-4.24 (m, 1H), 4.22-4.10 (m, 1H), 3.33 (d, J=6.0 Hz, 1H), 1.28-1.16 (m, 3H); $^{13}$C NMR (100 MHz, CDCl$_3$) δ 174.7, 137.1, 126.0, 123.9, 123.2, 120.8, 120.1, 114.5, 112.0, 68.0, 62.7, 14.8; HRMS (CI) m/z calcd. for (C$_{12}$H$_{13}$NO$_3$+Na$^+$): 242.0793. found: 242.0789; IR (CHCl$_3$) v 3406, 1733, 1458, 1201, 1078, 1048, 745 cm$^{-1}$. (+)-6Aa was obtained in 85% yield and 93% ee from a reaction catalyzed by QD-1d (10.0 mol %) at room temperature for 6 hours.

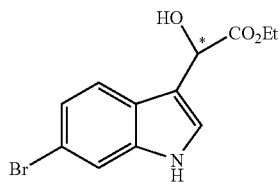

6Ea (−)-6Ea was obtained as a colorless oil in 96% yield after flash chromatography (elution solvent: ethyl acetate/hexanes=1/2) and 90% ee as determined by HPLC analysis [Daicel chiralcel OD+OD, hexanes:IPA, 90:10, 1.0 mL/min, λ 220 nm, t (major)=48.84 min, t (minor)=45.83 min] from a reaction catalyzed by Q-1d (10 mol %) at room temperature for 4 hours. $[\alpha]_D^{25}=-76.7$ (c 1.0, CHCl$_3$); $^1$H NMR (400 MHz, CDCl$_3$) δ 8.29 (br, 1H), 7.56 (d, J=8.8 Hz, 1H), 7.48 (d, J=1.6 Hz, 1H), 7.32 (dd, J=8.8 Hz, 1.6 Hz, 1H), 7.18 (d, J=2.4 Hz, 1H), 5.43 (d, J=4.8 Hz, 1H), 4.34-4.243 (m, 1H), 4.22-4.12 (m, 1H), 3.39 (d, J=4.8 Hz, 1H), 1.28-1.16 (m, 3H); $^{13}$C NMR (100 MHz, CDCl$_3$) δ 174.5, 137.9, 124.9, 124.1, 121.5, 116.8, 115.0, 114.7, 67.8, 62.9, 14.8; HRMS (CI) m/z calcd. for (C$_{12}$H$_{12}$BrNO$_3$+Na$^+$): 319.9898. found: 319.9891; IR (CHCl$_3$) v 3410, 1734, 1456, 1222, 1051, 805, 758 cm$^{-1}$. (+)-6Ea was obtained in 95% yield and 90% ee from a reaction catalyzed by QD-1d (10 mol %) at room temperature for 4 hours.

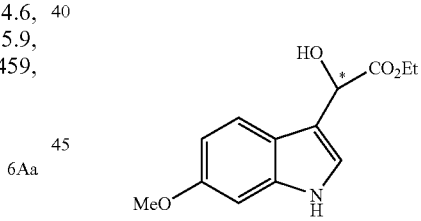

6Ba (−)-6Ba was obtained as a colorless oil in 94% yield after flash chromatography (elution solvent: ethyl acetate/hexanes=1/2) and 90% ee as determined by HPLC analysis [Daicel chiralcel OD, hexanes:IPA, 80:20, 1.0 mL/min, λ 220 nm, t (major)=16.00 min, t (minor)=14.59 min] from a reaction catalyzed by Q-1d (10 mol %) at room temperature for 4 hours. $[\alpha]_D^{25}=-85.1$ (c 0.8, CHCl$_3$); $^1$H NMR (400 MHz, CDCl$_3$) δ 8.13 (br, 1H), 7.57 (d, J=9.2 Hz, 1H), 7.10-7.06 (m, 1H), 6.83-6.78 (m, 2H), 5.42 (d, J=6.4 Hz, 1H), 4.34-4.24 (m, 1H), 4.22-4.12 (m, 1H), 3.82 (s, 3H), 3.33 (d, J=6.4 Hz, 1H), 1.25-1.12 (m, 3H); $^{13}$C NMR (100 MHz, CDCl$_3$) δ 174.3, 156.9, 137.5, 122.3, 120.3, 119.9, 114.0, 110.4, 94.9, 67.6, 62.3, 55.8, 14.3; HRMS (CI) m/z calcd. for (C$_{13}$H$_{15}$NO$_4$+H$^+$): 250.1079. found: 250.1071; IR (CHCl$_3$) v 3403, 2931, 1732, 1633, 1456, 1201, 1079, 808, 760 cm$^{-1}$. (+)-6Ba was obtained in 93% yield and 82% ee from a reaction catalyzed by QD-1d (10.0 mol %) at room temperature for 4 hours.

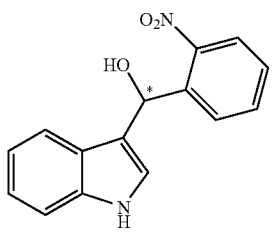
6Ab (−)-6Ab was obtained as a yellow solid in 96% yield after flash chromatography (elution solvent: ethyl acetate/hexanes=1/4) and 90% ee as determined by HPLC analysis [Daicel chiralcel OD, hexanes:IPA, 80:20, 1.0 mL/min, λ 220 nm, t (major)=14.6 min, t (minor)=18.6 min] from a reaction catalyzed by Q-1d (10 mol %) at room temperature for 72 hours. mp 215-217° C.; $[\alpha]_D^{25}$=−100.0 (c 0.9, Acetone); $^1$H NMR (400 MHz, Acetone-d$^6$) δ 10.13 (br, 1H), 8.09 (d, J=8.0 Hz, 1H), 7.84 (d, J=8.0 Hz, 1H), 7.72 (t, J=8.0 Hz, 1H), 7.58-7.48 (m, 2H), 7.35 (d, J=8.0 Hz, 1H), 7.07 (dt, J=1.2 Hz, 6.4 Hz, 1H), 6.98-6.92 (m, 2H), 6.79-6.72 (m, 1H), 4.87 (d, J=4.8, 1H); $^{13}$C NMR (100 MHz, Acetone-d$^6$) δ 148.9, 139.8, 137.2, 132.8, 128.9, 128.1, 126.5, 124.1, 136.6, 121.8, 119.7, 119.2, 118.0, 111.6, 64.8; HRMS (CI) m/z calcd. for ($C_{15}H_{12}N_2O_3$—OH): 251.0821. found: 251.0812; IR (CHCl$_3$) ν 3409, 1608, 1520, 1341, 1058, 745 cm$^{-1}$. (+)-6Ab was obtained in 95% yield and 89% ee from a reaction catalyzed by QD-1d (10.0 mol %) at room temperature for 72 hours.

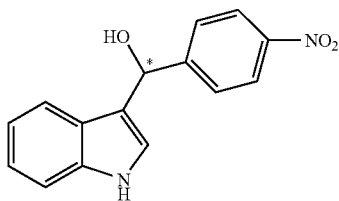
6Ac (+)-6Ac was obtained as a yellow solid in 90% yield after flash chromatography (elution solvent: ethyl acetate/hexanes=1/4) and 88% ee as determined by HPLC analysis [Daicel chiralcel OD, hexanes:IPA, 90:10, 1.0 mL/min, λ 220 nm, t (major)=85.6 min, t (minor)=101.4 min] from a reaction catalyzed by Q-1d (10 mol %) at room temperature for 72 hours. mp 162-163° C.; $[\alpha]_D^{25}$=53.8 (c 0.8, Acetone); $^1$H NMR (400 MHz, Acetone-d$^6$) δ 10.20 (br, 1H), 8.19 (d, J=8.4 Hz, 2H), 7.79 (d, J=8.4 Hz, 2H), 7.53 (d, J=8.0 Hz, 1H), 7.37 (d, J=8.0 Hz, 1H), 7.23-7.18 (m, 1H), 7.07 (t, J=7.2 Hz, 1H), 6.94 (t, J=7.2 Hz, 1H), 6.25 (d, J=4.0 Hz, 1H), 4.91 (d, J=4.0, 1H); $^{13}$C NMR (100 MHz, Acetone-d$^6$) δ 153.5, 147.0, 137.4, 127.6 (2C), 126.1, 123.4, 123.3 (2C), 121.8, 119.8, 119.2, 119.0, 111.6, 69.1; HRMS (CI) m/z calcd. for ($C_{15}H_{12}N_2O_3$—OH): 251.0821. found: 251.0815; IR (CHCl$_3$) ν 3370, 2924, 1593, 1514, 1343, 1071, 1000 cm$^{-1}$. (−)-6Ac was obtained in 90% yield and 83% ee from a reaction catalyzed by QD-1d (10 mol %) at room temperature for 72 hours.

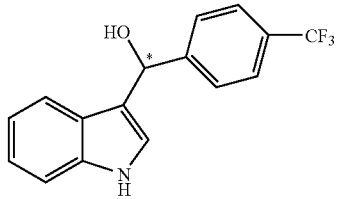
6Ad (+)-6Ad was obtained as a white solid in 85% yield after flash chromatography (elution solvent: ethyl acetate/hexanes=1/4) and 88% ee as determined by HPLC analysis [Daicel chiralcel OD, hexanes:IPA, 90:10, 1.0 mL/min, λ 220 nm, t (major)=42.0 min, t (minor)=45.7 min] from a reaction catalyzed by Q-1d (10 mol %) at room temperature for 72 hours. mp 111-112° C.; $[\alpha]_D^{25}$=+25.0 (c 0.8, CHCl$_3$); $^1$H NMR (400 MHz, CDCL$_3$) δ 8.11 (br, 1H), 7.66-7.54 (m, 5H), 7.37 (d, J=8.0 Hz, 1H), 7.22 (t, J=8.0 Hz, 1H), 7.11 (t, J=8.0 Hz, 1H), 6.96 (s, 1H), 6.21 (d, J=3.6 Hz, 1H), 2.30 (d, J=3.6 Hz, 1H); $^{13}$C NMR (100 MHz, CDCl$_3$) δ 148.0, 137.3, 127.3 (2C), 126.2, 125.94, 125.91, 125.87, 125.84, 123.6, 123.4, 120.8, 120.1, 119.7, 112.1, 70.3; HRMS (CI) m/z calcd. for ($C_{16}H_{12}F_3NO$—OH): 274.0844. found: 274.0833; IR (CHCl$_3$) ν 3399, 3225, 1606, 1328, 1118, 747 cm$^{-1}$. (−)-6Ad was obtained in 83% yield and 88% ee from a reaction catalyzed by QD-1d (10.0 mol %) at room temperature for 72 hours.

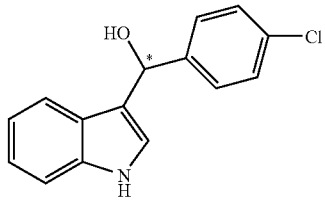
6Ae (+)-6Ae was obtained as a yellow solid in 75% yield after flash chromatography (elution solvent: ethyl acetate/hexanes=1/4) and 83% ee as determined by HPLC analysis [Daicel chiralcel OJ, hexanes:IPA, 80:20, 1.0 mL/min, λ 220 nm, t (major)=35.87 min, t (minor)=41.39 min] from a reaction catalyzed by Q-1d (10 mol %) at 70° C. for 40 hours. mp 88-90° C.; $[\alpha]_D^{25}$=+25.6 (c 0.8, CHCl$_3$); $^1$H NMR (400 MHz, Acetone-d6) δ 8.10 (br, 1H), 7.57 (d, J=8.0 Hz, 1H), 7.43 (d, J=8.0 Hz, 2H), 7.36 (d, J=8.0 Hz, 1H), 7.32 (d, J=8.0 Hz, 2H), 7.22 (t, J=8.0 Hz, 1H), 7.10 (t, J=8.0 Hz, 1H), 6.95 (d, J=2.0 Hz, 1H), 6.14 (d, J=2.8 Hz, 1H), 2.26 (d, J=2.8 Hz, 1H); $^{13}$C NMR (100 MHz, CDCl$_3$) δ 142.6, 137.3, 133.7, 129.1 (2C), 128.5 (2C), 126.2, 123.5, 123.3, 120.7, 120.2, 120.0, 112.0, 70.3; HRMS (CI) m/z calcd. for ($C_{15}H_{12}ClNO$—OH): 240.0580. found: 240.0575; IR (CHCl$_3$) ν 3408, 1684, 1490, 1457, 1090, 1013, 744 cm$^{-1}$.

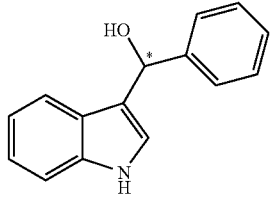
6Af (+)-6Af was obtained as a colorless oil in 60% yield after flash chromatography (elution solvent: ethyl acetate/hexanes=1/4) and 82% ee as determined by HPLC analysis [Daicel chiralcel OJ+OJ, hexanes:IPA, 70:30, 1.0 mL/min, λ 220 nm, t (major)=76.81 min, t (minor)=71.31 min] from a reaction catalyzed by Q-1d (10 mol %) at 70° C. for 48 hours. $[\alpha]_D^{25}$=+9.5 (c 0.7, $CHCl_3$); $^1$H NMR (400 MHz, $CDCl_3$) δ 8.07 (br, 1H), 7.62 (d, J=8.0 Hz, 2H), 7.51 (d, J=7.6 Hz, 2H), 7.43-7.27 (m, 4H), 7.23 (t, J=8.0 Hz, 1H), 7.10 (t, J=8.0 Hz, 1H), 6.98-6.94 (m, 1H), 6.19 (d, J=3.6 Hz, 1H), 2.23 (d, J=3.6 Hz, 1H); $^{13}$C NMR (100 MHz, $CDCl_3$) δ 144.2, 137.3, 129.0 (2C), 128.1, 127.2 (2C), 126.5, 123.4, 123.1, 120.6, 120.5, 120.3, 111.9, 71.0; HRMS (CI) m/z calcd. for ($C_{15}H_{13}NO$—OH): 206.0970. found: 206.0960; IR ($CHCl_3$) ν 3415, 3058, 1601, 1456, 1217, 1093, 744 $cm^{-1}$.

Example 4

X-Ray Analysis of (+)-4Dc Obtained with QD-1d

A colorless block crystal with dimensions 0.10×0.08×0.02 mm was mounted on a glass fiber using very small amount of paratone oil.

Data were collected using a Bruker SMART CCD (charge coupled device) based diffractometer equipped with an Oxford Cryostream low-temperature apparatus operating at 193 K. Obtained with graphite monochromated Mo Kα (λ=0.71073 Å) radiation; $R1=\Sigma||F_o|-|F_c||/\Sigma|F_o|$; $wR_2=\{\Sigma[w(F_o^2-F_c^2)^2/\{\Sigma[w(F_o^2)^2]\}^{1/2}$. Data were measured using omega scans of 0.3° per frame for 30 seconds, such that a hemisphere was collected. A total of 1271 frames were collected with a maximum resolution of 0.76 Å. The first 50 frames were recollected at the end of data collection to monitor for decay. Cell parameters were retrieved using SMART software and refined using SAINT on all observed reflections. SMART V 5.625 (NT) *Software for the CCD Detector System*; Bruker Analytical X-ray Systems, Madison, Wis. (2001). Data reduction was performed using the SAINT software which corrects for Lp and decay. SAINT V 6.22 (NT) *Software for the CCD Detector System* Bruker Analytical X-ray Systems, Madison, Wis. (2001). Absorption corrections were applied using SADABS multiscan technique, supplied by George Sheldrick. SADABS. Program for absorption corrections using Siemens CCD based on the method of Robert Blessing; Blessing, R. H. *Acta Cryst.* A51 1995, 33-38. The structures are solved by the direct method using the SHELXS-97 program and refined by least squares method on $F^2$, SHELXL-97, incorporated in SHELXTL-PC V 6.10. Sheldrick, G. M. SHELXS-90, *Program for the Solution of Crystal Structure*, University of Göttingen, Germany, 1990; Sheldrick, G. M. SHELXL-97, *Program for the Refinement of Crystal Structure*, University of Göttingen, Germany, 1997; and SHELXTL 6.1 (PC-Version), *Program library for Structure Solution and Molecular Graphics*; Bruker Analytical X-ray Systems, Madison, Wis. (2000).

Figure 5:
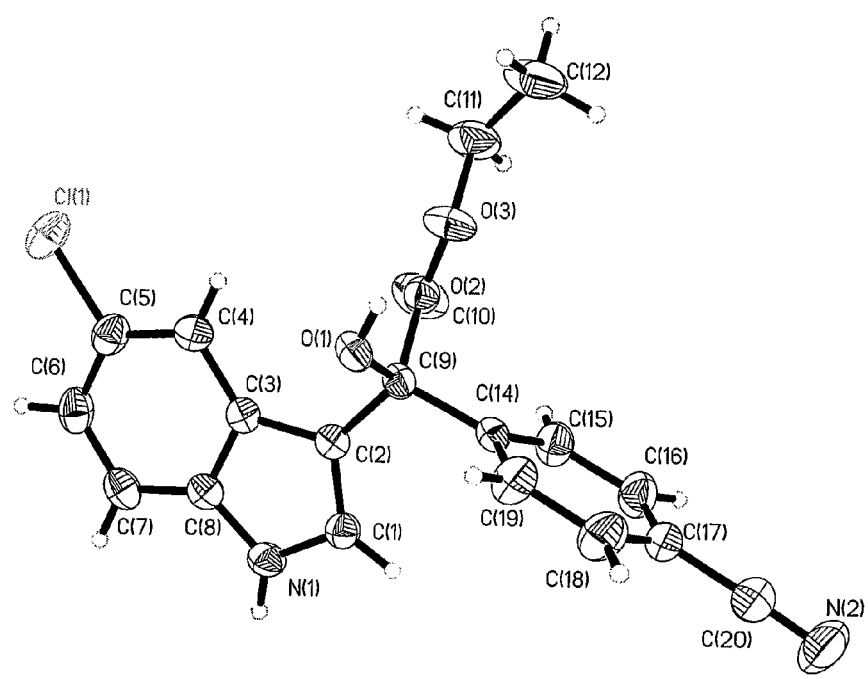
FIG. 5 depicts 50% thermal ellipsoidal drawings of the molecule (+)-4Dc in the asymmetric cell with various amount of labeling. The absolute configuration of (+)-4Dc which was obtained with QD-1d is S. See Example 4 for further details.
Figure 6:
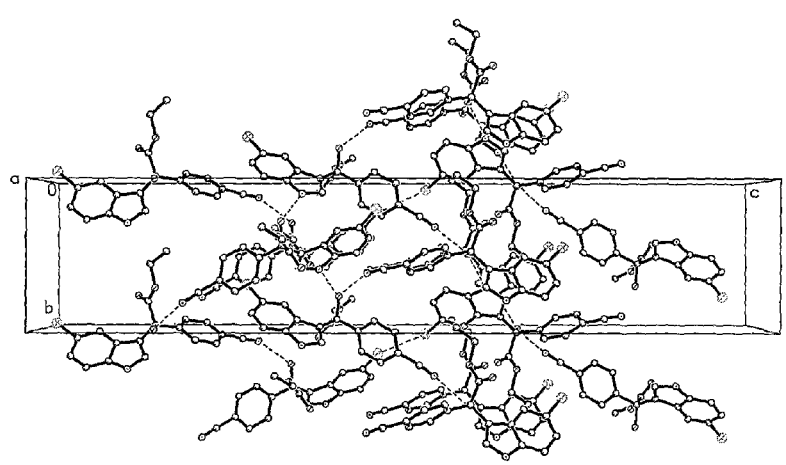
FIG. 6 depicts a drawing of the packing along the α-axis of the molecules (+)-4Dc with dotted lines showing hydrogen bonding scheme. See Example 4 for further details.
Figure 7:
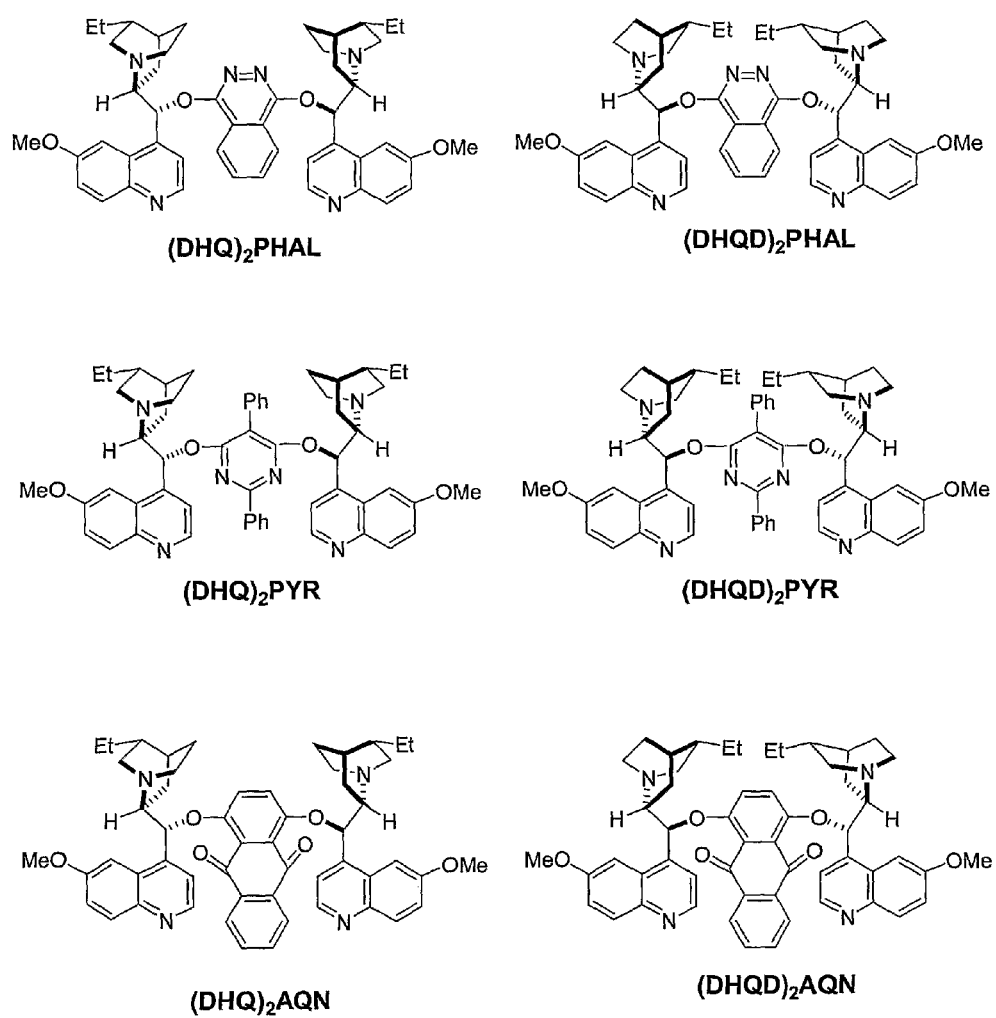
FIG. 7 depicts the structures of certain catalysts used in the methods of the present invention, and the abbreviations used herein for them.

The structure was solved in the space group $P4_32_12$ (#96) by analysis of systematic absences. All non-hydrogen atoms are refined anisotropically. Hydrogens were found by difference Fourier methods and refined isotropically. The Flack parameter is used to determine chirality of the crystal studied, the value should be near zero, a value of one is the other enantiomer and a value of 0.5 is racemic. Flack, H. D. Acta Cryst. A39, 1983, 876-881. The Flack parameter was refined to −0.05(7), confirming the absolute stereochemistry. The crystal used for the diffraction study showed no decomposition during data collection. All drawing are done at 50% ellipsoids. See FIGS. 5 and 6.

INCORPORATION BY REFERENCE

The U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of preparing a chiral, non-racemic alcohol from a prochiral aldehyde or prochiral ketone, comprising the step of:

reacting a prochiral aldehyde or prochiral ketone with an aromatic compound in the presence of a catalyst; thereby producing a chiral, non-racemic alcohol; wherein said aromatic compound is selected from the group consisting of

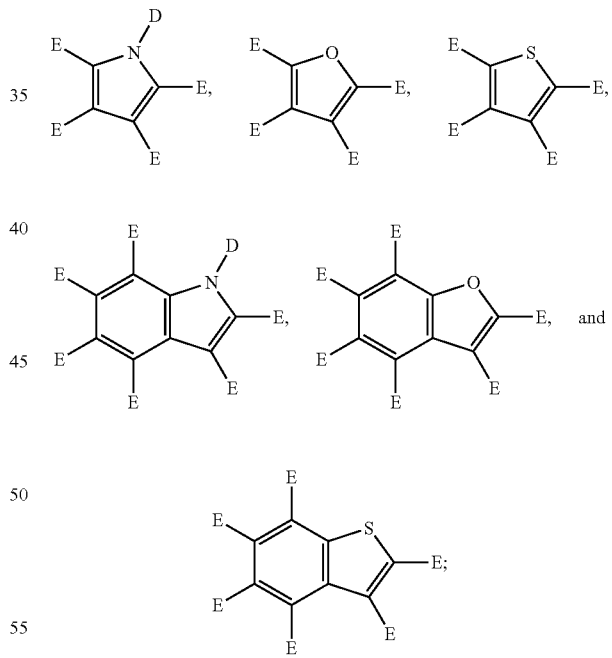

D is H, alkyl, aralkyl or acyl;

E is, independently for each occurrence, H, alkyl, alkenyl, aryl, cycloalkyl, aralkyl, heteroalkyl, halogen, hydroxy, cyano, amino, acyl, alkoxyl, nitro, thiol, amine, amido, phosphonate, phosphine, carboxyl, sulfonyl, ketone, aldehyde or ester;

said chiral, non-racemic alcohol has an enantiomeric excess or diastereomeric excess greater than about 70%; and said catalyst is
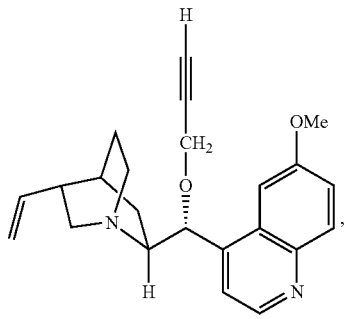
Q-PP
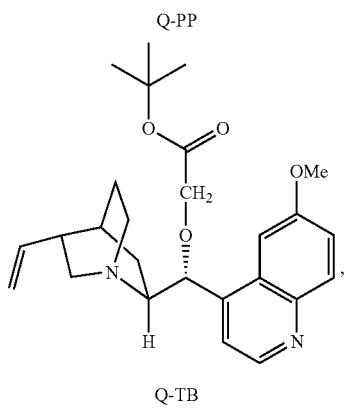
Q-TB
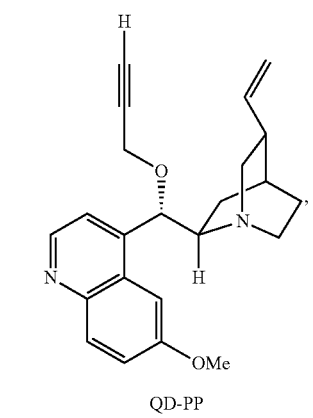
QD-PP
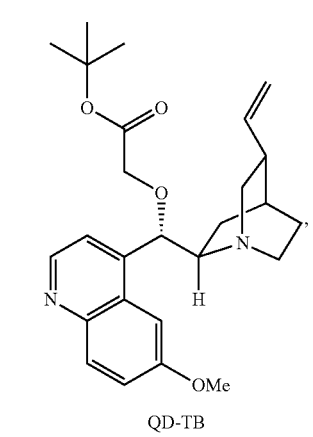
QD-TB
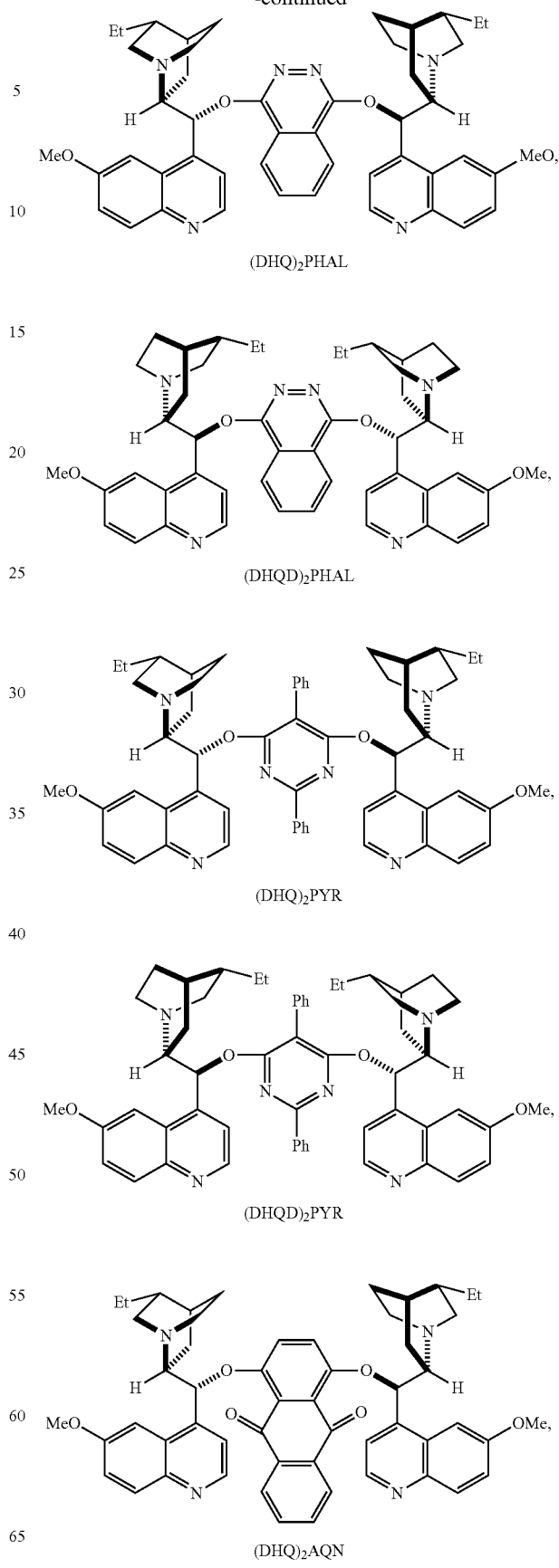

-continued

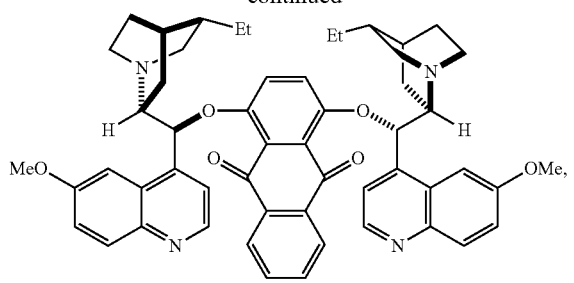

(DHQD)₂AQN

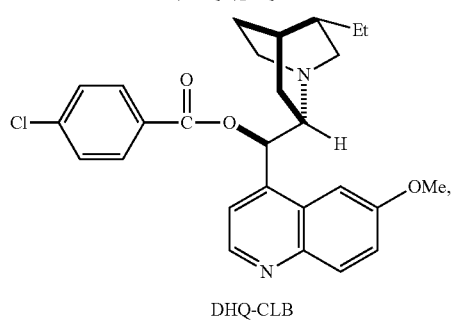

DHQ-CLB

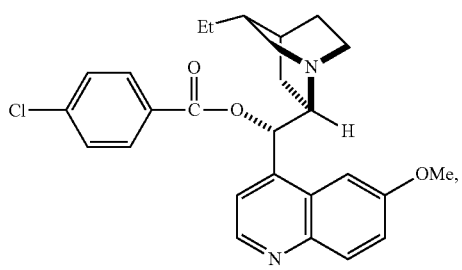

DHQD-CLB

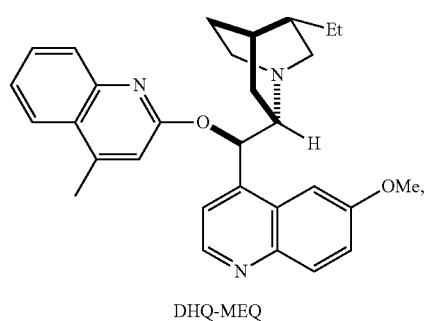

DHQ-MEQ

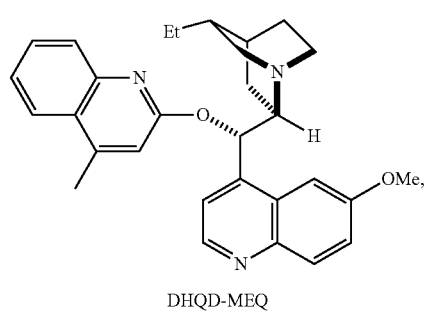

DHQD-MEQ

-continued

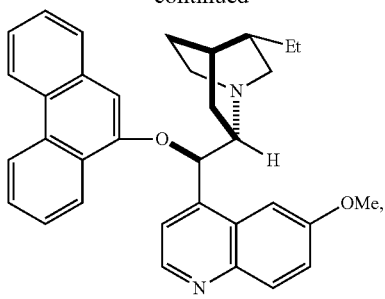

DHQ-AQN

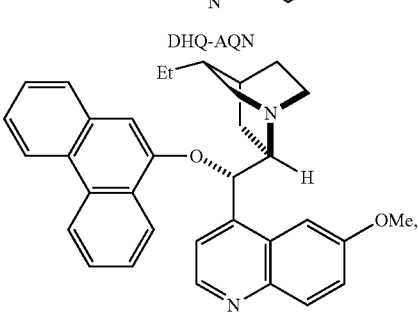

DHQD-AQN

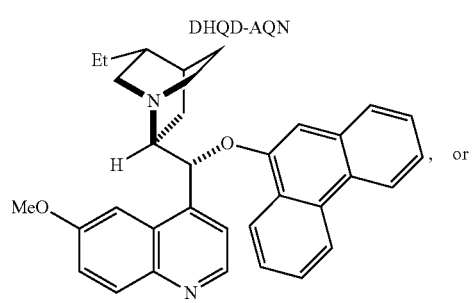

DHQ-PHN

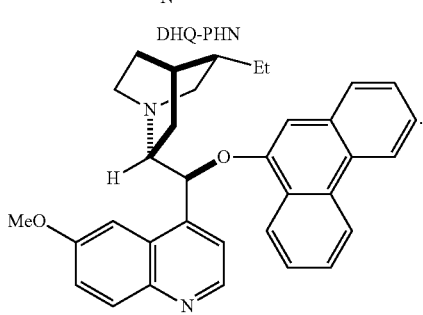

DHQD-PHN

2. A method of preparing a chiral, non-racemic alcohol from a prochiral aldehyde or prochiral ketone, comprising the step of:

reacting a prochiral aldehyde or prochiral ketone with an aromatic compound in the presence of a catalyst; thereby producing a chiral, non-racemic alcohol; wherein said aromatic compound is selected from the group consisting of

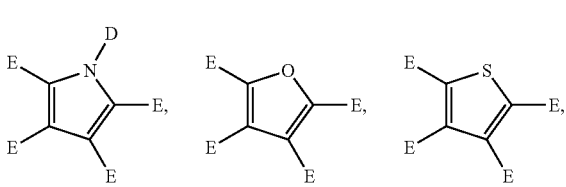

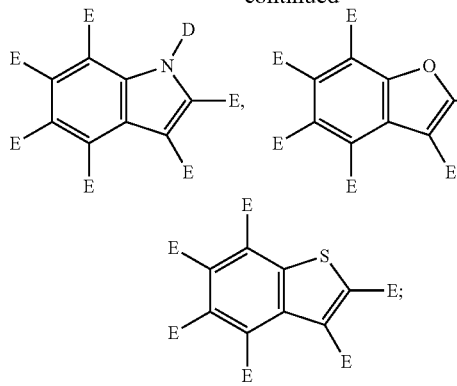

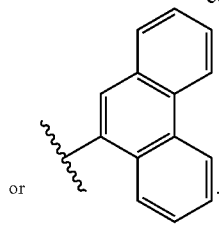

D is H, alkyl, aralkyl or acyl;

E is, independently for each occurrence, H, alkyl, alkenyl, aryl, cycloalkyl, aralkyl, heteroalkyl, halogen, hydroxy, cyano, amino, acyl, alkoxyl, nitro, thiol, amido, phosphonate, phosphine, carboxyl, sulfonyl, ketone, aldehyde or ester;

said chiral, non-racemic alcohol has an enantiomeric excess or diastereomeric excess greater than about 70%; and said catalyst is represented by formula I:

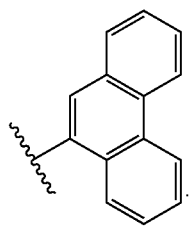

wherein, independently for each occurrence:

R represents alkyl, aryl, heteroaryl, aralkyl, heteroaralkyl, alkyloyl, aryloyl, arylalkyloyl, heteroaryloyl, or heteroarylalkyloyl;

$R_1$ represents alkyl, or alkenyl;

$R_2$ and $R_3$ represent alkyl, alkenyl, aryl, cycloalkyl, aralkyl, heteroalkyl, halogen, hydroxy, cyano, amino, acyl, alkoxyl, nitro, thiol, amido, phosphonate, phosphine, carboxyl, sulfonyl ketone, aldehyde, or ester;

n is an integer from 0 to 5 inclusive;

m is an integer from 0 to 8 inclusive;

$R_4$ represents —OH, —SH, or —$NHR_5$; and $R_5$ represents hydrogen, acyl or aralkyl.

3. The method of claim 2, wherein R represents aryl, aralkyl, or aryloyl.

4. The method of claim 2, wherein R represents

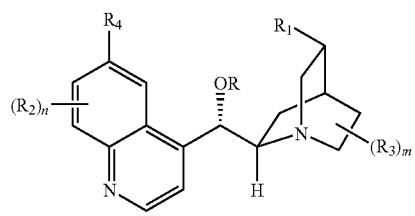

5. The method of claim 2, wherein R represents

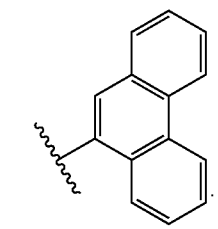 [SMILES: *c1cc2ccccc2c2ccccc12]

6. The method of claim 2, wherein n is 0.

7. The method of claim 2, wherein m is 0.

8. The method of claim 2, wherein R is aryl; and $R_1$ is —CH=$CH_2$.

9. The method of claim 2, wherein R is

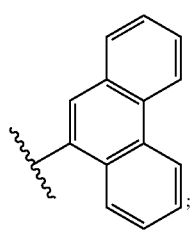 [SMILES: *c1cc2ccccc2c2ccccc12]

and $R_1$ is —CH=$CH_2$.

10. The method of claim 2, wherein R is aryl; $R_1$ is —CH=$CH_2$; m is 0; and n is 0.

11. The method of claim 2, wherein R is

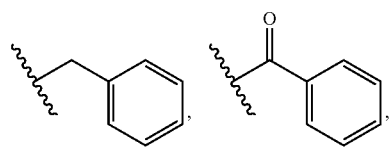

$R_1$ is —CH=$CH_2$; m is 0; and n is 0.

12. The method of claim 2, wherein said prochiral aldehyde or prochiral ketone is represented by III:

wherein
X represents alkyl, aryl, heteroaryl, aralkyl, or heteroaralkyl; and
Z represents H, perfluoroalkyl, alkyl, aryl, heteroaryl, aralkyl, or heteroaralkyl.

13. The method of claim 2, wherein said prochiral aldehyde or prochiral ketone is represented by IV:

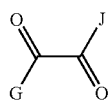

IV wherein
G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino;
J represents H, perfluoroalkyl, alkyl, aryl, heteroaryl, aralkyl, or heteroaralkyl; and
G and J may be connected by a covalent bond to form a 4, 5, 6, 7, or 8-membered ring.

14. The method of claim 1 or 2, wherein said aromatic compound is

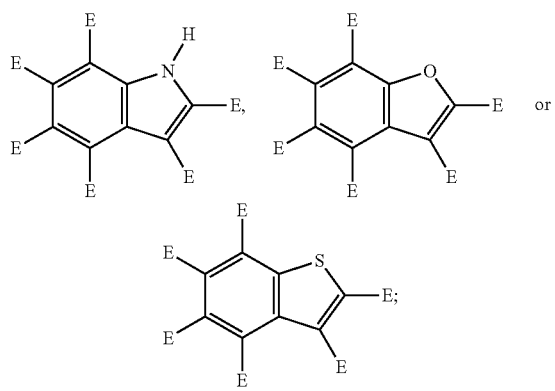

and E is, independently for each occurrence, H, alkyl, halogen or alkoxyl.

15. The method of claim 1 or 2, wherein said aromatic compound is

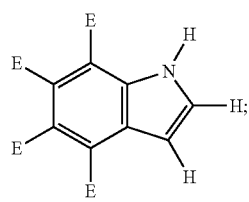

and E is, independently for each occurrence, H, alkyl, halogen or alkoxyl.

16. The method of claim 1 or 2, wherein said aromatic compound is selected from the group consisting of

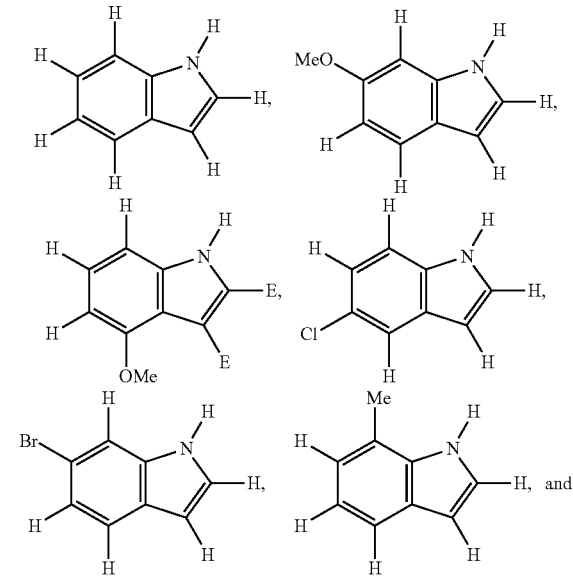

17. The method of claim 1 or 2, wherein said aromatic compound is

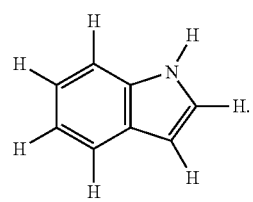

18. The method of claim 1 or 2, wherein said chiral, non-racemic alcohol has an enantiomeric excess or diastereomeric excess greater than about 90%.

19. The method of claim 1 or 2, wherein said chiral, non-racemic alcohol has an enantiomeric excess or diastereomeric excess greater than about 95%.

20. The method of claim 1 or 2, wherein the prochiral aldehyde or prochiral ketone, the aromatic compound, and the catalyst are reacted at room temperature.

* * * * *